US012700167B2

(12) United States Patent
Liu et al.

(10) Patent No.: US 12,700,167 B2
(45) Date of Patent: Aug. 4, 2026

(54) SLIT LAMP MICROSCOPE, OPHTHALMIC INFORMATION PROCESSING APPARATUS, OPHTHALMIC SYSTEM, METHOD OF CONTROLLING SLIT LAMP MICROSCOPE, AND RECORDING MEDIUM

(71) Applicant: Topcon Corporation, Tokyo (JP)

(72) Inventors: Jonathan Liu, Tokyo (JP); Hitoshi Shimizu, Tokyo (JP); Hisashi Tsukada, Hachioji (JP)

(73) Assignee: TOPCON CORPORATION, Tokyo (JP)

( * ) Notice: Subject to any disclaimer, the term of this patent is extended or adjusted under 35 U.S.C. 154(b) by 670 days.

(21) Appl. No.: 17/637,082

(22) PCT Filed: Jun. 2, 2020

(86) PCT No.: PCT/JP2020/021726
§ 371 (c)(1),
(2) Date: Feb. 22, 2022

(87) PCT Pub. No.: WO2021/049104
PCT Pub. Date: Mar. 18, 2021

(65) Prior Publication Data
US 2022/0280036 A1     Sep. 8, 2022

(30) Foreign Application Priority Data

Sep. 10, 2019     (JP) ................................. 2019-164262

(51) Int. Cl.
*G06T 15/08*       (2011.01)
*A61B 3/00*        (2006.01)
(Continued)

(52) U.S. Cl.
CPC ............ *G06T 15/08* (2013.01); *A61B 3/0008* (2013.01); *A61B 3/0025* (2013.01);
(Continued)

(58) Field of Classification Search
CPC ...................................................... A61B 3/135
See application file for complete search history.

(56) References Cited

U.S. PATENT DOCUMENTS 5,864,382 A     1/1999   Soya et al.
2002/0091321 A1     7/2002   Goldstein et al.
(Continued)

FOREIGN PATENT DOCUMENTS

CN     2595320 Y     12/2003
CN     104586350 A     5/2015
(Continued)

OTHER PUBLICATIONS

Office Action for Japanese Application No. JP 2019-164262, mailed Dec. 26, 2023, 4 pages (machine generated translation attached).
(Continued)

*Primary Examiner* — Peter K Huntsinger
(74) *Attorney, Agent, or Firm* — XSENSUS LLP

(57)     ABSTRACT

A slit lamp microscope of some aspect examples includes a scanner and a rendering processor. The scanner is configured to scan an anterior segment of a subject's eye with slit light to collect a plurality of cross sectional images. The rendering processor is configured to apply rendering to a three dimensional image created from the plurality of cross sectional images.

12 Claims, 17 Drawing Sheets

(51) Int. Cl.

| | |
|---|---|
| *A61B 3/10* | (2006.01) |
| *A61B 3/135* | (2006.01) |
| *A61B 3/14* | (2006.01) |
| *G06T 7/00* | (2017.01) |
| *G06T 7/11* | (2017.01) |

(52) U.S. Cl.

CPC .......... *A61B 3/0058* (2013.01); *A61B 3/0083* (2013.01); *A61B 3/102* (2013.01); *A61B 3/135* (2013.01); *A61B 3/14* (2013.01); *G06T 7/0012* (2013.01); *G06T 7/11* (2017.01); *G06T 2207/30041* (2013.01)

(56) References Cited

U.S. PATENT DOCUMENTS

| | | | |
|---|---|---|---|
| 2002/0182152 A1 | 12/2002 | Goldstein et al. | |
| 2003/0063258 A1 | 4/2003 | Torii et al. | |
| 2004/0152068 A1 | 8/2004 | Goldstein et al. | |
| 2005/0095653 A1 | 5/2005 | Goldstein et al. | |
| 2007/0038127 A1 | 2/2007 | Goldstein et al. | |
| 2015/0085252 A1 | 3/2015 | Fujimura et al. | |
| 2016/0345822 A1 | 12/2016 | Fujimura et al. | |
| 2017/0156591 A1* | 6/2017 | Berestka .............. | A61B 3/0083 |
| 2017/0251920 A1* | 9/2017 | Tokuda .................. | A61B 3/113 |
| 2019/0029514 A1 | 1/2019 | Tsukada et al. | |
| 2019/0209006 A1* | 7/2019 | Abou Shousha ...... | A61B 3/103 |
| 2019/0365218 A1* | 12/2019 | Okamoto ............. | A61B 3/0025 |
| 2020/0390330 A1 | 12/2020 | Fukuma et al. | |
| 2021/0153735 A1 | 5/2021 | Tsukada et al. | |

FOREIGN PATENT DOCUMENTS

| | | | | | |
|---|---|---|---|---|---|
| JP | | H1033482 A | 2/1998 | | |
| JP | | 2000-197607 A | 7/2000 | | |
| JP | | 2003-111728 A | 4/2003 | | |
| JP | | 2004-507296 A | 3/2004 | | |
| JP | | 2005-118076 A | 5/2005 | | |
| JP | | 2009-56149 A | 3/2009 | | |
| JP | | 2013-248376 A | 12/2013 | | |
| JP | | 2016-159073 A | 9/2016 | | |
| JP | | 2016-179004 A | 10/2016 | | |
| JP | | 2018-186930 A | 11/2018 | | |
| JP | | 2019-24618 A | 2/2019 | | |
| JP | | 2019-24738 A | 2/2019 | | |
| JP | | 2019042172 A | 3/2019 | | |
| JP | | 2019055134 A | 4/2019 | | |
| WO | WO-2013105915 A1 * | 7/2013 | ............. | A61B 3/135 |
| WO | 2019/176231 A1 | 9/2019 | | |

OTHER PUBLICATIONS

Decision of Refusal issued for the corresponding Japanese Patent Application No. 2019-164262, 2pp.

Decision of Dismissal of Amendment issued for the corresponding Japanese Patent Application No. 2019-164262, 4pp.

International Search Report and Written Opinion mailed on Aug. 18, 2020, received for PCT Application PCT/JP2020/021726, Filed on Jun. 2, 2020, 11 pages including English Translation.

Japanese Office Action issued Sep. 12, 2023 in corresponding Japanese Patent Application No. 2019-164262 (with machine-generated English translation), 8 pages.

Chinese Office Action issued Mar. 17, 2025, in corresponding Chinese Patent Application No. 202080062719.1.

Chinese Office Action issued Aug. 11, 2025, in corresponding Chinese Patent Application No. 202080062719.1, 28pp.

Japanese Decision in Trial issued Sep. 2, 2025, in corresponding Japanese Patent Application No. 2019-164262, 75pp.

* cited by examiner

SLIT LAMP MICROSCOPE, OPHTHALMIC INFORMATION PROCESSING APPARATUS, OPHTHALMIC SYSTEM, METHOD OF CONTROLLING SLIT LAMP MICROSCOPE, AND RECORDING MEDIUM

CROSS-REFERENCE TO RELATED APPLICATIONS

This application is a national stage (under 35 U.S.C. 371) of International Patent Application No. PCT/JP2020/021726, filed Jun. 2, 2020, claiming priority to Japanese Patent Application No. 2019-164262, filed Sep. 10, 2019, both of which are herein incorporated by reference in their entirety.

TECHNICAL FIELD

The present disclosure relates to a slit lamp microscope, an ophthalmic information processing apparatus, an ophthalmic system, a method of controlling a slit lamp microscope, and a recording medium.

BACKGROUND OF THE INVENTION

Diagnostic imaging serves an important role in the field of ophthalmology. Diagnostic imaging uses various kinds of ophthalmic imaging apparatuses. Types of examples of ophthalmic imaging apparatuses include a slit lamp microscope, a fundus camera, a scanning laser ophthalmoscope (SLO), an optical coherence tomography (OCT) apparatus, and the like.

A slit lamp microscope is the most widely and frequently utilized apparatuses among such various kinds of ophthalmic apparatuses. A slit lamp microscope is used for illuminating a subject's eye with slit light and observing and/or photographing the illuminated cross section from an oblique or side position with a microscope (see, for example, Japanese Unexamined Patent Application Publication No. 2016-159073, Japanese Unexamined Patent Application Publication No. 2016-179004, and Japanese Unexamined Patent Application Publication No. 2009-56149).

One of the main uses of a slit lamp microscope is observation of anterior eye segments. When observing an anterior eye segment, a doctor observes an entire anterior eye segment while moving the focal position and the area illuminated by slit light, thereby determining the presence or absence of abnormality. Further, a slit lamp microscope may also be used for prescription of vision correction devices such as for checking of a fitting state of a contact lens.

Diaphanoscopy (or red reflection technique) may be used for anterior eye segment observation (see, for example, Japanese Unexamined Patent Application Publication No. 2009-56149). Diaphanoscopy is an observation technique that uses retinal reflection of illumination light to depict intraocular conditions, and is typically a technique of depicting an opaque area of the crystalline lens as a shadow formed by the light beam reverting from the retina. An image obtained by diaphanoscopy is referred to as a transillumination image (diaphanoscopic image, red reflex image). While diaphanoscopy is a common technique widely used in the observation of cataract eyes, it has the following problems.

First, it is difficult to manage or control the brightness of transillumination images because diaphanoscopy uses the reflected light coming from the retina, and it is also difficult to manage (control, adjust) its image quality. These difficulties make diaphanoscopy unsuitable for quantitative diagnosis. Therefore, diagnosis using diaphanoscopy is highly dependent on the subjectivity of a person who conducts image interpretation, and for example, grade of cataract cannot be objectively evaluated. In addition, although automatic image analysis techniques using analysis programs or machine learning have been rapidly developing in recent years, the difficulty in image quality management is still one of the factors that prevent the application of automatic image analysis to transillumination images.

Second, a transillumination image is a planar image (projection image) with the eye fundus as a secondary light source, and has no information in the depth direction (axial direction, Z direction), which makes it impossible to provide opacity distribution in a three dimensional manner. In other words, a transillumination image only provides opacity distribution in the XY plane perpendicular to the Z direction, and cannot provide opacity distribution in the Z direction.

BRIEF SUMMARY OF THE INVENTION

An object of the present disclosure is to provide a novel ophthalmic observation technique without the drawbacks of diaphanoscopy.

A slit lamp microscope of some aspect examples may include a scanner configured to scan an anterior segment of a subject's eye with slit light to collect a plurality of cross sectional images, and a rendering processor configured to apply rendering to a three dimensional image created from the plurality of cross sectional images. In a slit lamp microscope of some aspect examples, the rendering processor may be configured to apply projection onto a predetermined plane to the three dimensional image. In a slit lamp microscope of some aspect examples, the predetermined plane may be perpendicular to a depth direction of the subject's eye. A slit lamp microscope of some aspect examples may further include a reconstruction processor configured to apply three dimensional reconstruction to the plurality of cross sectional images collected by the scanner, and a segmentation processor configured to apply segmentation to a three dimensional reconstructed image constructed by the reconstruction processor for setting the three dimensional image. In a slit lamp microscope of some aspect examples, the segmentation processor may be configured to identify a crystalline lens region from the three dimensional reconstructed image, and the three dimensional image may include at least part of the crystalline lens region. In a slit lamp microscope of some aspect examples, the rendering processor may be configured to apply the rendering to the crystalline lens region. In a slit lamp microscope of some aspect examples, the segmentation processor may be configured to apply segmentation to the crystalline lens region to identify a partial region that has a dimension in a depth direction of the subject's eye, and the rendering processor may be configured to apply the rendering to the partial region. In a slit lamp microscope of some aspect examples, the segmentation processor may be configured to identify at least one region of a capsule region and a nucleus region from the crystalline lens region, and then identify the partial region based on the at least one region. In a slit lamp microscope of some aspect examples, the scanner may include an illumination system configured to project the slit light onto the anterior segment, a photography system configured to perform photography of the anterior segment from a direction different from the illumination system, and a movement mechanism configured to move the illumination system and the photography system. In a slit lamp microscope of some aspect examples, the photography system may include an optical system configured to direct light coming from the anterior segment onto which the slit light is projected, and an image sensor including a light detecting plane configured to receive the light directed by the optical system, wherein a subject plane along an optical axis of the illumination system, the optical system, and the light detecting plane may satisfy a Scheimpflug condition. A slit lamp microscope of some aspect examples may further include a display device that displays a rendered image constructed by the rendering processor.

An ophthalmic information processing apparatus of some aspect examples may include a reception device that receives a plurality of cross sectional images collected by scanning an anterior segment of a subject's eye with slit light, and a rendering processor configured to apply rendering to a three dimensional image created from the plurality of cross sectional images.

An ophthalmic system of some aspect examples may include a slit lamp microscope, an information processing apparatus, and an image interpretation computer terminal. The slit lamp microscope may include a scanner configured to scan an anterior segment of a subject's eye with slit light to collect a plurality of cross sectional images, and a transmission device that transmits first transmission information that includes at least the plurality of cross sectional images collected by the scanner to the information processing apparatus via a communication line. The information processing apparatus may include a reception device that receives the first transmission information, a memory in which the first transmission information is stored, and a transmission device that transmits second transmission information that includes at least the plurality of cross sectional images included in the first transmission information to the image interpretation computer terminal via a communication line. The image interpretation computer terminal may include a reception device that receives the second transmission information, a rendering processor configured to apply rendering to a three dimensional image created from the plurality of cross sectional images included in the second transmission information, a user interface operated by a user to perform interpretation of a rendered image constructed by the rendering processor, and a transmission device that transmits third transmission information that includes at least information input using the user interface to the information processing apparatus via a communication line. The information processing apparatus may receive the third transmission information by the reception device thereof, associate the third transmission information with the first transmission information, and store the third transmission information in the memory.

An ophthalmic system of some aspect examples may include a slit lamp microscope, an information processing apparatus, and an image interpretation apparatus. The slit lamp microscope may include a scanner configured to scan an anterior segment of a subject's eye with slit light to collect a plurality of cross sectional images, and a transmission device that transmits first transmission information that includes at least the plurality of cross sectional images collected by the scanner to the information processing apparatus via a communication line. The information processing apparatus may include a reception device that receives the first transmission information, a memory in which the first transmission information is stored, and a transmission device that transmits second transmission information that includes at least the plurality of cross sectional images included in the first transmission information to the image interpretation apparatus via a communication line. The image interpretation apparatus may include a reception device that receives the second transmission information, a rendering processor configured to apply rendering to a three dimensional image created from the plurality of cross sectional images included in the second transmission information, an image interpretation processor configured to perform interpretation of a rendered image constructed by the rendering processor, and a transmission device that transmits fourth transmission information that includes at least information generated by the image interpretation processor to the information processing apparatus via a communication line. The information processing apparatus may receive the fourth transmission information by the reception device thereof, associate the fourth transmission information with the first transmission information, and store the fourth transmission information in the memory.

A method of some aspect examples is a method of controlling a slit lamp microscope that includes a processor, and a scanner that scans an anterior segment of a subject's eye with slit light to collect a plurality of cross sectional images. The method may include causing the processor to execute a process of applying rendering to a three dimensional image created from the plurality of cross sectional images corrected by the scanner.

A program of some aspect examples is configured to cause a computer to execute a method of any of aspect examples. A recording medium of some aspect examples is a computer-readable non-transitory recording medium in which a program of any of aspect examples is stored.

DETAILED DESCRIPTION OF THE INVENTION

Figure 1:
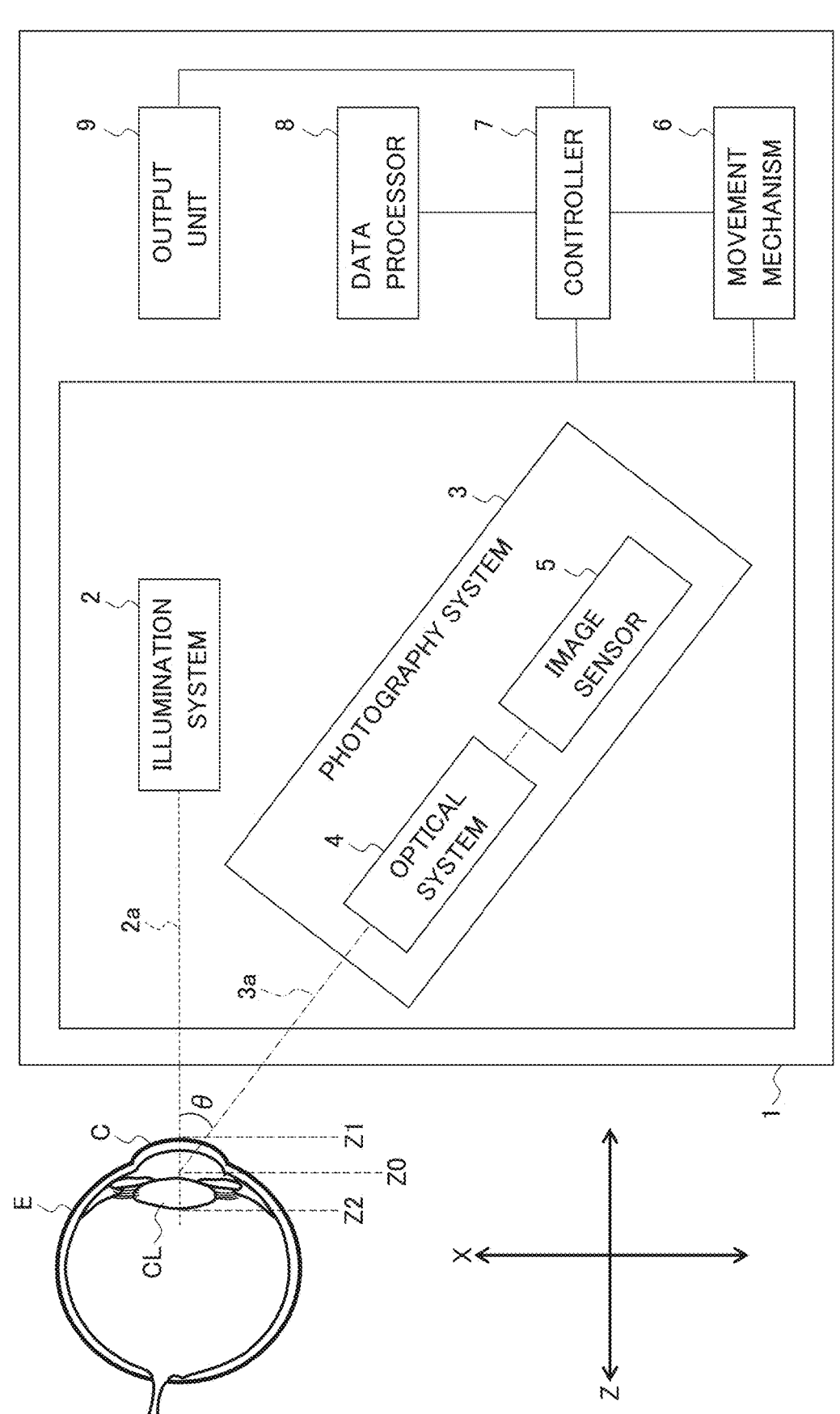
FIG. 1 is a schematic diagram illustrating the configuration of the slit lamp microscope of the aspect example.

Some aspect examples will be described in detail with referring to the drawings. It should be noted that any known techniques or technologies such as any of the matters or items disclosed in the documents cited herein may be combined with or incorporated in the aspect examples.

The slit lamp microscope of some aspect examples may be a stationary type or a portable type. The slit lamp microscope of some aspect examples has a (automatic) scanning function of scanning an anterior eye segment with slit light to acquire a plurality of cross sectional images, and is typically used in situations and/or environments where no technical experts (skilled persons) relating to the apparatus is present nearby. Note that the slit lamp microscope of some aspect examples may be used in situations and/or environments where a skilled person is present, or in situations and/or environments where a skilled person can provide monitoring, give instructions, and/or conduct an apparatus operation, from a remote place.

Examples of the facility in which the slit lamp microscope is installed include an optician's store, an optometrist's office, a health facility, a medical institution, a health check and screening venue, a patient's home, a welfare facility, a public facility, a medical examination vehicle, and the like.

The slit lamp microscope of some aspect examples is an ophthalmic imaging apparatus having at least the function of a slit lamp microscope, and may be further provided with any other photographing or imaging functions performed by other modality apparatuses. Examples of such other modality apparatuses include an anterior segment camera, a fundus camera (retinal camera), an SLO, an OCT apparatus, and the like. The slit lamp microscope of some aspect examples may further have any of the functions of measuring characteristics of eyes. Examples of such measurement functions include visual acuity measurement, refraction measurement, intraocular pressure measurement, corneal endothelial cell measurement, aberration measurement, visual field measurement, and the like. The slit lamp microscope of some aspect examples may further include application software for analyzing photographed images, measurement data, or the like. The slit lamp microscope of some aspect examples may further include any of the functions for treatment or surgery. Examples of such treatment or surgery includes photocoagulation treatment and photodynamic therapy.

The ophthalmic information processing apparatus of some aspect examples includes a processor (circuit, circuitry) that processes a plurality of cross sectional images collected by a slit lamp microscope having the scanning function described above. The ophthalmic information processing apparatus of some aspect examples may be a peripheral device of the slit lamp microscope, may be connected to the slit lamp microscope through a local area network (LAN), or may be connected to the slit lamp microscope through a wide area network. Alternatively, the ophthalmic information processing apparatus of some aspect examples may have a function of accepting (receiving) input of a plurality of cross sectional images stored in a recording medium.

The ophthalmic system of some aspect examples (the first ophthalmic system) may include one or more slit lamp microscopes, one or more information processing apparatuses, and one or more image interpretation computer terminals, and may be used for telemedicine, for example. The slit lamp microscope may be a slit lamp microscope of any aspect example, or may be a slit lamp microscope including at least part of a slit lamp microscope of any aspect example.

The information processing apparatus is configured to receive an image acquired by the slit lamp microscope and transmit the image to the image interpretation computer terminal. In addition, the information processing apparatus may have a function of managing images acquired by the slit lamp microscope(s).

The image interpretation computer terminal is a computer used by a doctor (typically, a specialist such as an ophthalmologist or a medical image interpreter) to conduct interpretation of an image acquired by the slit lamp microscope. Here, the interpretation is an act of observing an image to obtain medical findings. Information entered into the image interpretation computer terminal by the person who has conducted the image interpretation may, for example, be converted by the image interpretation computer terminal or another computer into an image interpretation report or electronic medical record information and then transmitted to the information processing apparatus. In some other examples, information entered into the image interpretation computer terminal by a person who conducts image interpretation may be transmitted to the information processing apparatus. In this case, the information processing apparatus or another computer may perform conversion of the information entered by the person who conducts the image interpretation into an image interpretation report or electronic medical record information. The information processing apparatus may be configured to perform management of image interpretation reports or electronic medical record information by itself, or to transfer (forward, send) image interpretation reports or electronic medical record information to another medical system (e.g., an electronic medical record system).

An ophthalmic system of another aspect example (the second ophthalmic system) may include one or more slit lamp microscopes, one or more information processing apparatuses, and one or more image interpretation apparatuses. At least one of the slit lamp microscope and the information processing apparatus may be the same as or similar to that (those) of the first ophthalmic system.

The image interpretation apparatus is a computer configured to perform interpretation of an image acquired by the slit lamp microscope, using an image processing processor and/or an artificial intelligence engine, for example. Information derived from the image by the image interpretation apparatus may be converted by the image interpretation apparatus or another computer into an image interpretation report or electronic medical record information and then transmitted to the information processing apparatus, for example. In some other examples, information derived from the image by the image interpretation apparatus may be transmitted to the information processing apparatus. In this case, the information processing apparatus or another computer may convert the information derived from the image by the image interpretation apparatus into an image interpretation report or electronic medical record information. The information processing apparatus may be configured to perform management of image interpretation reports or electronic medical record information by itself, or to transfer (forward, send) image interpretation reports or electronic medical record information to another medical system.

As described thus far, the slit lamp microscopes, the ophthalmic information processing apparatuses, and the ophthalmic systems of some aspect examples can be used for telemedicine. On the other hand, acquisition of an adequate image (good image, satisfactory image) using a conventional slit lamp microscope is not an easy task. In addition, effective image interpretation and diagnosis requires acquisition of an image of a wide area of an anterior eye segment "in advance". For these reasons, it can be said that effective telemedicine using slit lamp microscopes has not been achieved. Some aspect examples can provide technologies and techniques that contributes to the achievement (realization, implementation) of effective telemedicine with slit lamp microscopes. Some aspect examples may also be applied for other uses.

Hereinafter, some aspect examples will be described. Any two or more of these aspect examples may be combined at least in part. Further, any modifications, such as additions, replacements, and/or omissions, on the basis of any known technique or technology, may be applied to such a combination.

The "processor" as used in the aspect examples described below includes a circuit or circuitry such as a central processing unit (CPU), a graphics processing unit (GPU), an application specific integrated circuit (ASIC), or a programmable logic device (PLD). Examples of the PLD include a simple programmable logic device (SPLD), a complex programmable logic device (CPLD), and a field programmable gate array (FPGA). For example, the processor loads and executes a program or data stored in a memory circuit or a storage for implementing the functions of a corresponding aspect example. The processor may include a circuit (circuitry) used for artificial intelligence or cognitive computing. The processor of some typical examples may include a computer system trained and configured through machine learning.

First Aspect Example

FIG. 1 shows an example of the slit lamp microscope of the first aspect example.

The slit lamp microscope 1 may be used for photographing the anterior segment of the subject's eye E, and includes the illumination system 2, the photography system 3, the movement mechanism 6, the controller 7, the data processor 8, and the output unit 9. The cornea of the subject's eye E is denoted by the reference character C, and the crystalline lens is denoted by the reference character CL.

The slit lamp microscope 1 may be a single apparatus, or may also be a system that includes two or more apparatuses. In the case where the slit lamp microscope 1 is configured as a system, the slit lamp microscope 1 may include a main apparatus, a computer, and a communication device. Here, the main apparatus may include the illumination system 2, the photography system 3, and the movement mechanism 6, the computer may include the controller 7, the data processor 8, and the output unit 9, and the communication device may perform communication between the main apparatus and the computer. In another case where the slit lamp microscope 1 is configured as a system, the slit lamp microscope 1 may include a main apparatus, a computer, an output device, and a communication device. Here, the main apparatus may include the illumination system 2, the photography system 3, and the movement mechanism 6, the computer may include the controller 7 and the data processor 8, the output device may include the output unit 9, and the communication device may perform communication among the main apparatus, the computer, and the output device. The computer of some examples may be installed together with the main apparatus or may also be installed on a network. The same applies to the output device.

<Illumination System 2>

The illumination system 2 projects slit light onto the anterior segment of the subject's eye E. The reference character 2a denotes the optical axis of the illumination system 2 that is referred to as the illumination optical axis. The illumination system 2 may have the same or similar configuration as or to the illumination system of a conventional slit lamp microscope. For example, the illumination system 2 includes an illumination light source, a positive lens, a slit forming member, and an objective lens in the order from the side far from the subject's eye E (not shown in the drawings).

The illumination light source outputs (emits) illumination light. The illumination system 2 may include a plurality of illumination light sources. For example, the illumination system 2 may include both an illumination light source that outputs continuous light or steady light, and an illumination light source that outputs flash light. Further, the illumination system 2 may include both an illumination light source for anterior segment illumination and an illumination light source for posterior segment illumination. Furthermore, the illumination system 2 may include two or more illumination light sources with mutually different output wavelengths. A typical example of the illumination system 2 includes a visible light source as an illumination light source. The illumination system 2 may also include an infrared light source. The illumination light output from the illumination light source passes through the positive lens and is projected onto the slit forming member.

The slit forming member passes a part of the illumination light to generate slit light. A typical example of the slit forming member has a pair of slit blades. The width of the region through which the illumination light passes is changed by changing the interval between the slit blades, and the width of the slit light is changed accordingly. The region through which the illumination light passes is referred to as a slit, and the interval between the slit blades is referred to as a slit width. Further, the slit forming member may be configured to be capable of changing the length of the slit light. The length of the slit light is a size of a cross section of the slit light along the direction perpendicular to the cross sectional width direction of the slit light. Here, the cross sectional width direction corresponds to the slit width. The width of the slit light and the length of the slit light of some typical examples are represented as the size of a projected image on the anterior segment formed by the slit light, however, possible representations of the width and length of the slit light are not limited to these. For example, the width of the slit light and the length of the slit light may be represented as the size of the cross section of the slit light at a freely selected position, or as the size of the slit formed by the slit forming member.

The slit light generated by the slit forming member is refracted by the objective lens and is projected onto the anterior segment of the subject's eye E.

The illumination system 2 may further include a focus mechanism configured for changing the focal position of the slit light. The focus mechanism may be configured to move the objective lens along the illumination optical axis 2a, for example. The movement of the objective lens may be carried out automatically and/or manually. Another focus mechanism may be configured to change the focal position of the slit light by: preparing and disposing a focusing lens at a position in the illumination optical axis 2a between the objective lens and the slit forming member, and moving the focusing lens along the illumination optical axis 2a.

Note that FIG. 1 is a top view. As shown in FIG. 1, the direction along the axis of the subject's eye E is defined as the Z direction in the present aspect example. Of the directions perpendicular to the Z direction, the left-right direction (or, the lateral direction) for the subject is defined as the X direction. The direction perpendicular to both the X direction and the Z direction is defined as the Y direction. In some typical examples, the X direction is the direction from one of the left eye and the right eye toward the other, and the Y direction is the direction parallel to the body axis of the subject (body axis direction).

<Photography System 3>

The photography system 3 is configured to perform photography of the anterior segment while the slit light from the illumination system 2 is being projected onto the anterior segment. The reference character 3a denotes the optical axis of the photography system 3 that is referred to as the photography optical axis. The photography system 3 of the present aspect example includes the optical system 4 and the image sensor 5.

The optical system 4 is configured to direct light coming from the anterior segment of the subject's eye E onto which the slit light is being projected, to the image sensor 5. The image sensor 5 includes a light detecting plane that receives the light directed by the optical system 4.

The light directed by the optical system 4, that is, the light coming from the anterior segment of the subject's eye E, contains return light of the slit light being projected onto the anterior segment, and may further contain other kinds of light. Examples of the return light include reflected light of the slit light, scattered light of the slit light, and fluorescence induced by the slit light. Examples of the other kinds of light include light from the environment in which the slit lamp microscope 1 is installed, such as indoor light (room light) and sunlight. In the case where another illumination system different from the illumination system 2 is provided as an anterior segment illumination system for illuminating the entire anterior segment, return light of the anterior segment illumination light emitted by the anterior segment illumination system may be contained in the light directed by the optical system 4.

The image sensor 5 may be an area sensor that has a two dimensional image detecting area. The image sensor 5 may be, for example, a charge-coupled device (CCD) image sensor, a complementary metal oxide semiconductor (CMOS) image sensor, or another type of image sensor.

The optical system 4 may have, for example, the same or similar configuration as or to the photography system of a conventional slit lamp microscope. For example, the optical system 4 includes an objective lens, a variable magnification optical system, and an imaging lens in the order from the side closer to the subject's eye E. The light coming from the anterior segment of the subject's eye E onto which the slit light is being projected, passes through the objective lens and the variable magnification optical system, and then forms an image on the light detecting plane of the image sensor 5 by the imaging lens.

The photography system 3 may include the first photography system and the second photography system, for example. In a typical example, the first photography system and the second photography system have the same configuration. The case in which the photography system 3 includes the first photography system and the second photography system will be described later as another aspect example.

The photography system 3 may further include a focus mechanism configured for changing the focal position of the photography system 3. The focus mechanism may be configured to move the objective lens along the photography optical axis 3a, for example. The movement of the objective lens may be carried out automatically and/or manually. Note that a focusing lens may be prepared and disposed at a position in the photography optical axis 3a between the objective lens and the imaging lens, and also the focus mechanism may be capable of moving the focusing lens along the photography optical axis 3a, thereby changing the focal position of the photography system 3.

The illumination system 2 and the photography system 3 function as a Scheimpflug camera. More specifically, the illumination system 2 and the photography system 3 are configured in such a manner that the subject plane along the illumination optical axis 2a, the optical system 4, and the light detecting plane of the image sensor 5 satisfy what is commonly referred to as the Scheimpflug condition. More specifically, the YZ plane passing through the illumination optical axis 2a (the YZ plane contains the subject plane), the principal plane of the optical system 4, and the light detecting plane of the image sensor 5 intersect on the same straight line. As a result of this, photographing can be performed with all positions in the subject plane in focus. In other words, photographing can be performed with all positions in the direction along the illumination optical axis 2a in focus.

The illumination system 2 and the photography system 3 of the present aspect example are configured in such a manner that at least an area defined by the anterior surface of the cornea C and the posterior surface of the crystalline lens CL is in focus of the photography system 3, for example. In other words, photography may be performed in a state in which the focus of the photography system 3 is on the entire area from the apex of the anterior surface of the cornea C (Z=Z1) to the apex of the posterior surface of the crystalline lens CL (Z=Z2) shown in FIG. 1. Note that the location Z=Z0 corresponds to the Z coordinate of the intersection of the illumination optical axis 2a and the photography optical axis 3a.

The condition described above is typically implemented by the configuration and arrangement of the elements included in the illumination system 2, the configuration and arrangement of the elements included in the photography system 3, and the relative positions between the illumination system 2 and the photography system 3. A parameter indicating the relative positions of the illumination system 2 and the photography system 3 may include the angle θ formed by the illumination optical axis 2a and the photography optical axis 3a, for example. The value of the angle θ may be set to 17.5 degrees, 30 degrees, or 45 degrees, for example. The angle θ may be variable.

<Movement Mechanism 6>

The movement mechanism 6 is configured to move the illumination system 2 and the photography system 3. The movement mechanism 6 includes, for example, a movable stage, an actuator, and a mechanism. The illumination system 2 and the photography system 3 are placed on the movable stage. The actuator is configured to operate in accordance with a control signal input from the controller 7. The mechanism is configured to receive driving force generated by the actuator and move the movable stage. In some other examples, the movement mechanism 6 may include a movable stage on which the illumination system 2 and the photography system 3 are placed, and a mechanism configured to receive force applied to an operation device (not shown in the drawings) and move the movable stage. The operation device is a lever, for example. The movable stage may be movable at least in the X direction and may be further movable in at least one of the Y direction and the Z direction.

The movement mechanism 6 of the present aspect example is configured to move the illumination system 2 and the photography system 3 together with each other in the X direction, for example. In other words, the movement mechanism 6 moves the illumination system 2 and the photography system 3 in the X direction while maintaining the state in which the above-mentioned Scheimpflug condition is satisfied. In parallel with this movement, the photography system 3 performs moving image photography at a predetermined time interval (photographing rate, acquisition rate), for example. As a result of this, a three dimensional area of the anterior segment of the subject's eye E is scanned with the slit light, and a plurality of images (a cross sectional image group) corresponding to the plurality of cross sections in the three dimensional area are collected.

<Controller 7>

The controller 7 is configured to control each part of the slit lamp microscope 1. For example, the controller 7 controls elements of the illumination system 2 (e.g., illumination light source, slit forming member, focus mechanism, etc.), elements of the photography system 3 (e.g., focus mechanism, image sensor, etc.), the movement mechanism 6, the data processor 8, and the output unit 9, and the like. Further, the controller 7 may be capable of executing control for changing the relative positions of the illumination system 2 and the photography system 3.

The controller 7 includes a processor, a primary storage, a secondary storage, and the like. The secondary storage stores a control program and the like. The control program and the like may be stored in a computer or a storage accessible by the slit lamp microscope 1. The function of the controller 7 is implemented by cooperation of software such as the control program and hardware such as the processor.

The controller 7 may be capable of applying the following controls to the illumination system 2, the photography system 3 and the movement mechanism 6 in order to perform scanning on a three dimensional area of the anterior segment of the subject's eye E with the slit light.

Figure 2A:
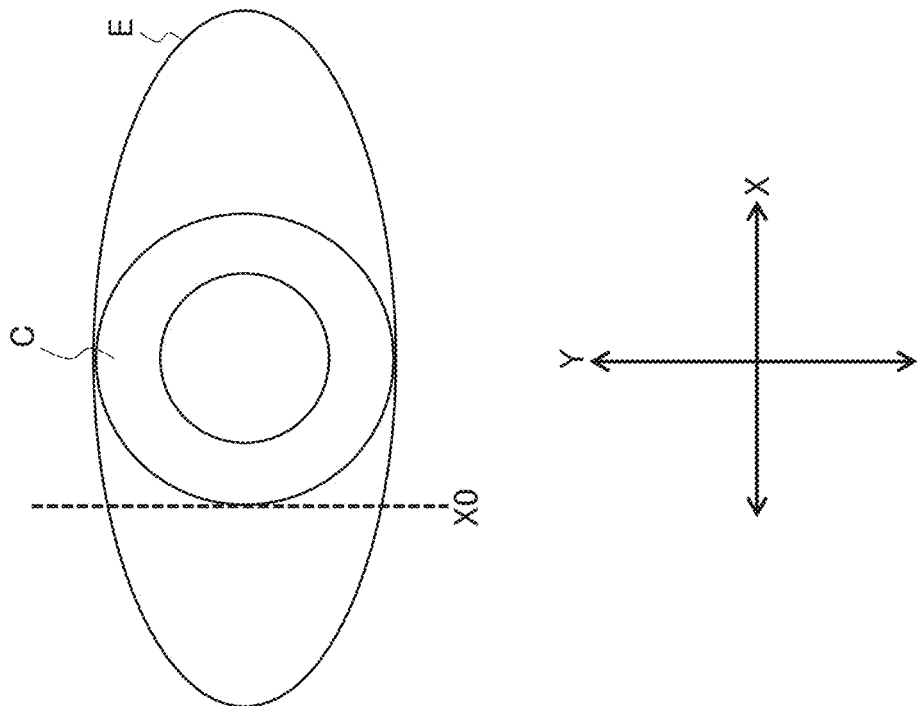
FIG. 2A is a schematic diagram for describing the operation of the slit lamp microscope of the aspect example.
Figure 2B:
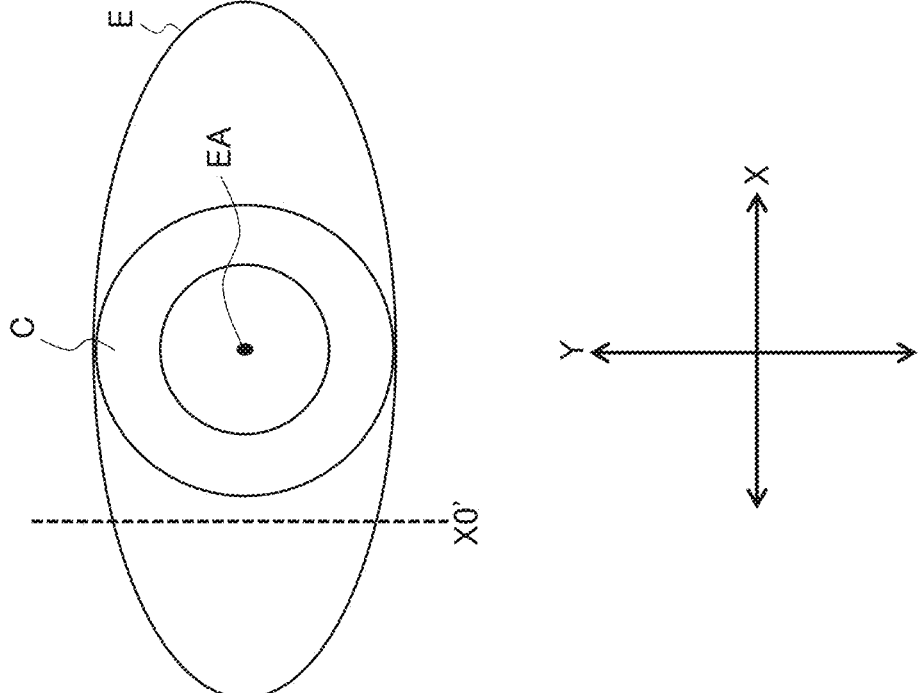
FIG. 2B is a schematic diagram for describing the operation of the slit lamp microscope of the aspect example.

First, the controller 7 controls the movement mechanism 6 to place the illumination system 2 and the photography system 3 at a predetermined scan start position. This control is referred to as alignment control. The scan start position is, for example, a position corresponding to the edge position (first edge position) of the cornea C in the X direction, or a position further away from the axis of the subject's eye E than the first edge position. The reference character X0 shown in FIG. 2A denotes an example of a scan start position corresponding to the first edge position of the cornea C in the X direction. Further, the reference character X0' shown in FIG. 2B denotes an example of a scan start position further away from the axis EA of the subject's eye E than the position corresponding to the first edge position of the cornea C in the X direction.

The controller 7 controls the illumination system 2 to start the projection of the slit light onto the anterior segment of subject's eye E. This control is referred to as slit light projection control. The slit light projection control may be performed before the execution of the alignment control or during the execution of the alignment control. The slit light is typically continuous light, but the slit light may be intermittent light (pulse light). The turning on/off control of the pulse light is synchronized with the photographing rate of the photography system 3. The slit light is typically visible light, but the slit light may be infrared light or a mixture of visible light and infrared light.

The controller 7 controls the photography system 3 to start moving image photography (moving image acquisition) of the anterior segment of the subject's eye E. This control is referred to as photography control. The photography control may be performed before the execution of the alignment control or during the execution of the alignment control. In some typical examples, the photography control is executed simultaneously with the slit light projection control or after the slit light projection control.

After having executed the alignment control, the slit light projection control, and the photography control, the controller 7 performs control of the movement mechanism 6 to start the movement of the illumination system 2 and the photography system 3. This control is referred to as movement control. The illumination system 2 and the photography system 3 are moved together by the movement control. In other words, the movement mechanism 6 moves the illumination system 2 and the photography system 3 while maintaining the relative positions (e.g., the angle θ) between the illumination system 2 and the photography system 3. In some typical examples, the movement mechanism 6 moves the illumination system 2 and the photography system 3 while maintaining the state in which the aforementioned Scheimpflug condition is satisfied. The movement of the illumination system 2 and the photography system 3 is performed from the aforementioned scan start position to a predetermined scan end position. The scan end position is, for example, a position corresponding to the edge position (second edge position) of the cornea C on the opposite side of the first edge position in the X direction, or a position further away from the axis of the subject's eye E than the second edge position, as in the scan start position. In such a case, the area from the scan start position to the scan end position becomes a scan area.

In some typical examples, the photography system 3 carries out the moving image photography in parallel with the projection of the slit light onto the anterior segment and the movement of the illumination system 2 and the photography system 3 in the X direction. The width direction of the slit light corresponds to the X direction and the longitudinal direction of the slit light corresponds to the Y direction.

Here, the length of the slit light (that is, the size of the slit light in the Y direction) is set to be, for example, equal to or greater than the diameter of the cornea C on the surface of the subject's eye E. In other words, the length of the slit light is set to be equal to or greater than the corneal diameter in the Y direction. Further, the distance of the movement of the illumination system 2 and the photography system 3 carried out by the movement mechanism 6 (that is, scan area) is set to be equal to or greater than the corneal diameter in the X direction, as described above. As a result of setting the slit light length and the movement distance in these manners, an area including the entire cornea C can be scanned with the slit light.

Figure 3:
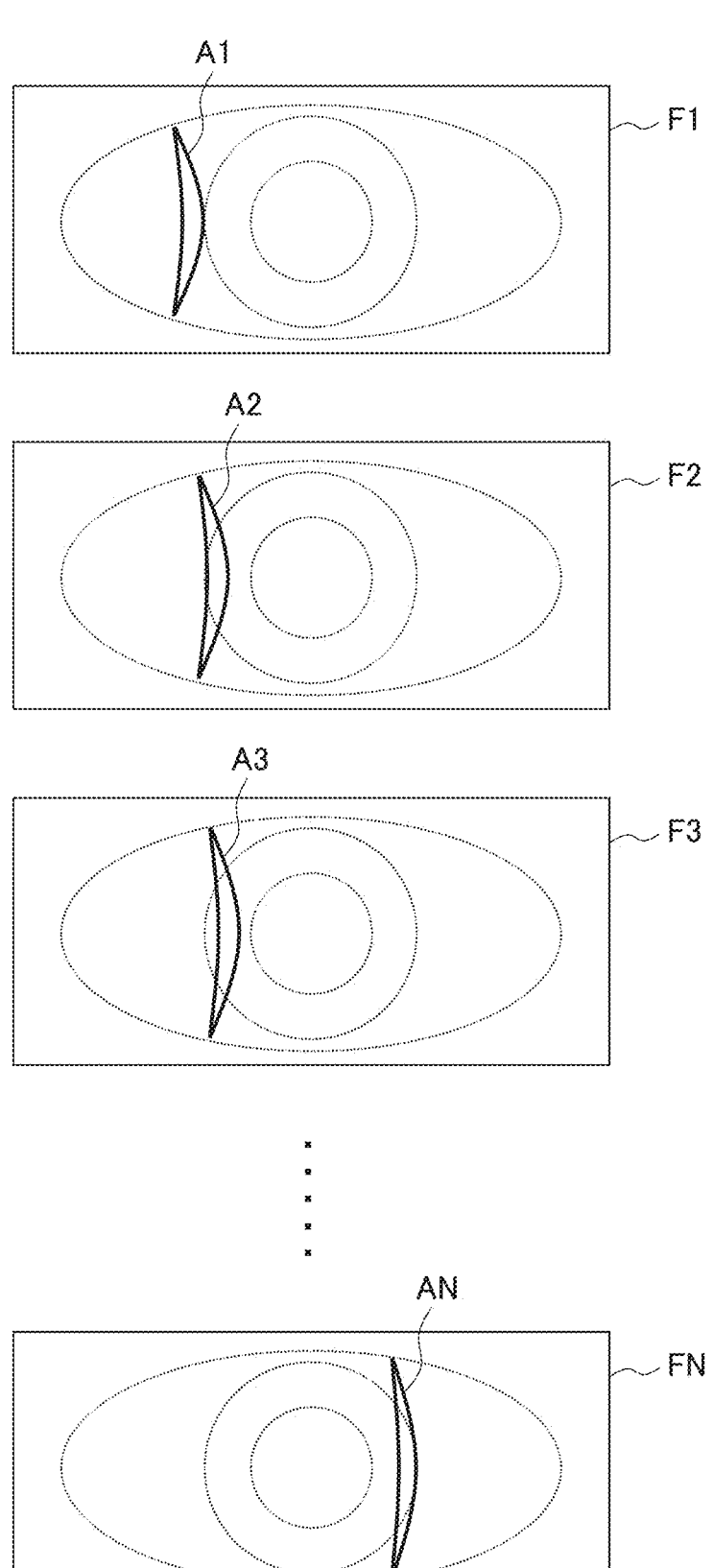
FIG. 3 is a schematic diagram for describing the operation of the slit lamp microscope of the aspect example.

With such a scan, a plurality of anterior segment images corresponding to mutually different slit light projection positions is acquired. In other words, a moving image is obtained in which the state (aspect) of the movement of the slit light projection position in the X direction is depicted. In the present aspect example, since the Scheimpflug condition is satisfied, a plurality of cross sectional images can be obtained in which a slit light projected region (cross section) at the time of photographing (at the time of capturing) is depicted in high definition. FIG. 3 shows an example of such a plurality of anterior segment images, that is, an example of such a group of frames (a frame group) composing a moving image.

FIG. 3 shows the plurality of anterior segment images (the frame group, the cross sectional image group) F1, F2, F3, . . . , and FN. The subscripts "n" of the anterior segment images Fn (n=1, 2, . . . , N) represent a time series order. In other words, the n-th anterior segment image acquired is represented by the reference character "Fn". The anterior segment image Fn includes the region onto which the slit light is being projected (slit light projected region) An. As shown in FIG. 3, the positions of the slit light projected regions A1, A2, A3, . . . , and AN shift to the right in time series order. The scan start position and the scan end position in the example shown in FIG. 3 correspond to both edge positions of the cornea C in the X direction. Possible scan start positions and/or possible scan end positions are not limited to the present example. The scan start position and/or the scan end position may be a position(s) further away from the axis of the subject's eye E than the edge position(s) of the cornea, for example. In addition, the direction of scans and the number of (times of) scans may be set accordingly.

<Data Processor 8>

The data processor 8 executes various kinds of data processing. Data to be processed may be either any data acquired by the slit lamp microscope 1 or any data input from the outside. For example, the data processor 8 can process images acquired by using the photography system 3. Note that the configuration examples and the function examples of the data processor 8 will also be described in other aspect examples in addition to the description of the present aspect example.

The data processor 8 includes a processor, a primary storage, a secondary storage, and the like. The secondary storage stores a data processing program and the like. The data processing program and the like may be stored in a computer or a storage accessible by the slit lamp microscope 1. The function of the data processor 8 is implemented by cooperation of software such as the data processing program and hardware such as the processor.

Figure 4A:
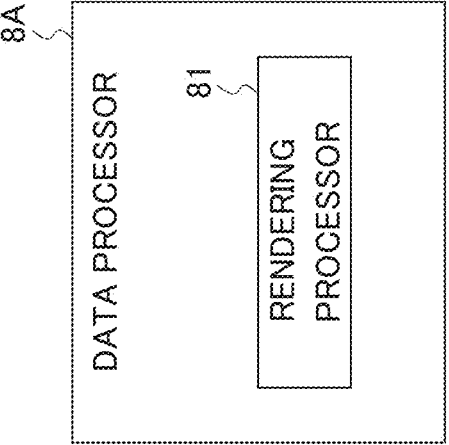
FIG. 4A is a schematic diagram illustrating the configuration of the slit lamp microscope of the aspect example.
Figure 4B:
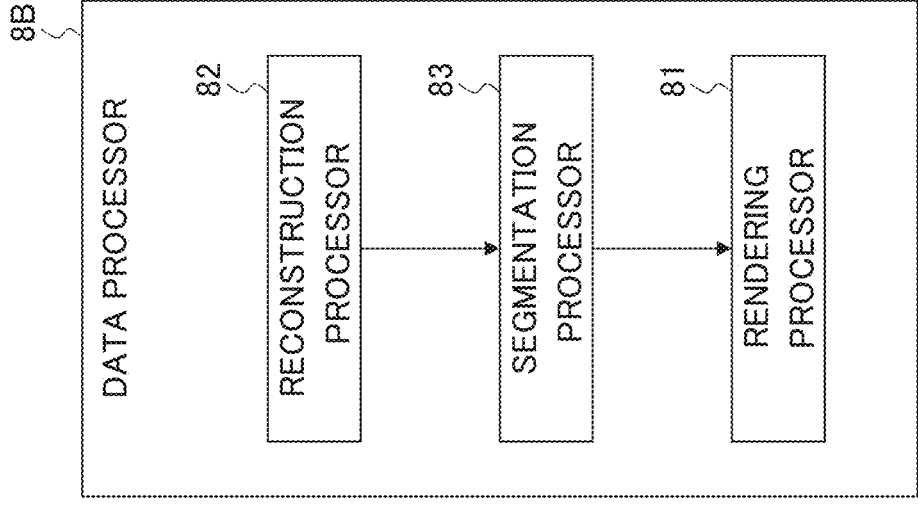
FIG. 4B is a schematic diagram illustrating the configuration of the slit lamp microscope of the aspect example.

Some examples of the data processor 8 will be described. FIG. 4A and FIG. 4B show the data processors 8A and 8B, which are the first and second examples of the data processor 8, respectively. The configuration of the data processor 8 is not limited to these examples. The data processor 8 of some examples may include a freely selected element for achieving the same or similar results as these examples.

The data processor 8A shown in FIG. 4A includes the rendering processor 81. The rendering processor 81 is configured to apply rendering to a three dimensional image constructed based on the plurality of anterior segment images collected by the aforementioned scanning.

The three dimensional image to which the rendering is to be applied is an image whose pixel positions are defined using a three dimensional coordinate system. The three dimensional image of some examples is a part of a three dimensional reconstructed image of a plurality of anterior segment images or the entire three dimensional reconstructed image. The three dimensional reconstructed image of some examples may be stack data or volume data.

Stack data is constructed by representing, using a single three dimensional coordinate system (three dimensional image space), a plurality of anterior segment images defined by mutually different two dimensional coordinate systems (two dimensional image spaces). In other words, stack data is constructed by embedding a plurality of anterior segment images in the same three dimensional image space. For example, the embedding positions of individual anterior segment images may be determined based on the relative positional relationship between the plurality of anterior segment images.

In some examples, the relative positional relationship between the plurality of anterior segment images may be determined from the content of the above-mentioned scan control (slit light projection control, photography control, movement control, etc.). As an example of this, the relative positional relationship (arrangement intervals, etc.) of the plurality of anterior segment images can be determined based on the content of the movement control (scan area) and the content of the photography control (photographing rate, acquisition rate, capture rate, frame rate).

In some other examples, front images of the anterior segment are collected in parallel with scanning for collecting a plurality of cross sectional images of the anterior segment (a plurality of anterior segment images). In some typical examples, this anterior segment front photographing is synchronized with this scanning, and the relative positional relationship between the plurality of cross sectional images can be determined from the slit light projection regions depicted in the plurality of front images.

Volume data is also referred to as voxel data, and is constructed by applying a known voxelization process to stack data in some typical examples. It should be noted that the three dimensional image in the present aspect example is not limited to stack data or volume data.

The rendering processor 81 applies rendering to the three dimensional image obtained in this way. Examples of the technique of this rendering include volume rendering, surface rendering, maximum intensity projection (MIP), minimum intensity projection (MinIP), and multi planar reconstruction (MPR). The rendering technique applied to the present aspect example is mainly projection.

The projection includes image processing of executing a projection (integration), in a predetermined direction, of a group of pixels (pixel group) included in the three dimensional image. In other words, the projection includes image processing of projecting a group of images (image group) included in the three dimensional image onto a predetermined plane. In some typical examples, the rendering processor 81 can construct a two dimensional image (projection image) defined in the XY coordinate system by applying projection in the Z direction to the three dimensional image defined in the XYZ coordinate system.

Needless to say, it is also possible to employ any rendering technique other than projection. The rendering processor 81 of some examples may be prepared as being capable of executing a plurality of kinds of rendering techniques, and these techniques may be executed in a selective manner.

The data processor 8B shown in FIG. 4B includes the reconstruction processor 82 and the segmentation processor 83 in addition to the same or similar rendering processor 81 as or to the data processor 8A.

The reconstruction processor 82 is configured to apply three dimensional reconstruction to the plurality of anterior segment images collected by the above-mentioned scanning. With this, a three dimensional reconstructed image is created from the plurality of anterior segment images. A three dimensional reconstructed image of some typical examples is stack data or volume data.

The three dimensional reconstruction technique applied to this three dimensional reconstructed image generation is freely selected. In some typical examples, the reconstruction processor 82 may apply a known three dimensional reconstruction technique to the plurality of anterior images in order to construct stack data. Further, the reconstruction processor 82 may apply a known voxelization process to this stack data in order to construct volume data.

The reconstruction processor 82 is configured to be capable of executing any of known processing executable as a part of three dimensional reconstruction and known processing executable together with three dimensional reconstruction. For example, the reconstruction processor 82 may apply, to the plurality of anterior segment images and/or the three dimensional reconstructed image, freely-selected correction processing such as noise elimination, brightness correction, distortion correction, contrast correction, color correction, and gamma correction. In addition, the reconstruction processor 82 may apply, to the plurality of anterior segment images and/or the three dimensional reconstructed image, a freely-selected filter such as a moving average filter, a Gaussian filter, a median filter, a Sobel filter, a smoothing filter, a sharpening filter, and a thinning filter.

The segmentation processor 83 is configured to apply segmentation to the three dimensional reconstructed image (stack data, volume data, etc.) constructed by the reconstruction processor 82. Segmentation or image segmentation is a process of partitioning an image into a plurality of segments (a plurality of regions). The segmentation of the present aspect example is used for identifying a partial region of the three dimensional reconstructed image.

The segmentation technique applicable to the present aspect example may be freely selected. The segmentation processor 83 of some examples includes a processor that operates in accordance with a program for executing a known segmentation algorithm. The segmentation processor 83 of some other examples may include an artificial intelligence engine. In some typical examples, this artificial intelligence engine may include a convolutional neural network (CNN). This convolutional neural network may have been trained in advance using training data that includes a large number of images acquired with slit lamp microscopes and corresponding segmentation results.

The segmentation processor 83 of some examples may be configured to identify an image region corresponding to a predetermined tissue (predetermined site, part, or area) from the three dimensional reconstructed image constructed by the reconstruction processor 82. This tissue to be identified may usually be any tissue that can be photographed by the slit lamp microscope 1. For example, the tissue to be identified may be any of the followings: the cornea; a sub-tissue of the cornea (such as the anterior surface of the cornea, posterior surface of the cornea, corneal epithelium, Bowman's layer, corneal stroma, Dua's layer, Descemet's membrane, corneal endothelium); the iris; the anterior surface of the iris; the pupil; the anterior chamber; the crystalline lens; a sub-tissue of the crystalline lens (such as the anterior surface of the crystalline lens, posterior surface of the crystalline lens, crystalline lens epithelium, crystalline lens capsule); the vitreous body; a lesion; a blood vessel; and other ocular tissues.

Further, the segmentation processor 83 may be configured to identify an image region corresponding to any part of any ocular tissue from the three dimensional reconstructed image constructed by the reconstruction processor 82. For example, this part to be identified may be, for example, any of the front part (anterior part), central part, back part (posterior part), edge part, end part, and other parts.

As mentioned above, diaphanoscopy has disadvantages that the brightness of an image cannot be controlled and that three dimensional information cannot be provided. One of the purposes of the slit lamp microscope 1 is to provide a novel crystalline lens observation technique without these disadvantages.

In order to achieve this purpose, the segmentation processor 83 may be configured to identify an image region corresponding to the crystalline lens (crystalline lens region) from the three dimensional reconstructed image constructed by the reconstruction processor 82.

In the case where the crystalline lens region is identified by the segmentation processor 83, at least a part of this crystalline lens region is set (determined, identified, specified) in the three dimensional image to which rendering will be applied by the rendering processor 81.

The rendering processor 81 of some examples may be configured to apply rendering to the entire crystalline lens region identified by the segmentation processor 83. In this case, a rendered image representing the entire crystalline lens region in the three dimensional reconstructed image constructed by the reconstruction processor 82, is obtained.

In some typical examples of the present aspect example, the slit light is visible light, so that the region behind the iris and the backside of the iris are not depicted in the plurality of anterior segment images collected by scanning. Therefore, the crystalline lens region in the three dimensional reconstructed image is only the image region corresponding to the part of the crystalline lens of the subject's eye E which is located just behind the pupil.

Further, because the slit lamp microscope 1 is configured to perform photography of a cross section illuminated by the slit light (e.g., YZ cross section) from an oblique angle, the state of this cross section is depicted in an anterior segment image obtained by photographing this cross section, and, in particular, a two dimensional distribution of opacities (opaque areas) in the crystalline lens (e.g., a distribution in the YZ direction or the YZ plane) is depicted. Repeating photography (photographing, image capturing) in parallel with moving such a cross section (e.g., performing moving image photography while performing movement of such a YZ cross section in the X direction) yields a three dimensional reconstructed image representing a three dimensional distribution of opaque areas in the crystalline lens. By applying segmentation to this three dimensional reconstructed image, a crystalline lens region including information on the three dimensional opacity distribution can be obtained.

The rendering processor 81 can apply projection in the Z direction (projection onto the XY plane) to this crystalline lens region. This projection constructs a projection image defined by the XY coordinate system. The projection in the Z direction includes the integration (addition) of the pixel values of a pixel group aligned along the Z direction, so that a projection image constructed thereby contains information regarding the positions (locations) and the states (conditions) of opacities in the crystalline lens.

The projection image constructed in this way not only represents the two dimensional opacity distribution (distribution in the XY plane) like a transillumination image, but also contains information on the opacity distribution (opacity distribution information) in the depth direction (Z direction, axial direction) inherited from the three dimensional reconstructed image.

In the case of displaying a projection image as a two dimensional image (planar image) like a transillumination image, information about the depth direction cannot be displayed spatially. Therefore, the depth information of individual opaque areas may be represented by display colors, display densities, display patterns, or like display parameters. For example, in the case of representing depths by colors, information indicating the correspondence between depths and colors (color bar) can be displayed together with a projection image.

The depth information of opaque areas may include information indicating any position of an opaque area such as the position of the most anterior part of an opaque area (the position closest to the cornea), the position of the most posterior part of an opaque area, or the central position of an opaque area. Further, the depth information of opaque areas may include information indicating the size of an opaque area in the depth direction.

When two or more opaque areas are arranged in the depth direction and overlap with each other, the depth information of these opaque areas may be displayed together, or the individual pieces of depth information of these opaque areas may be displayed in a selective manner.

In addition, information indicating the degree of opacity may be displayed. The degree of opacity may include information such as the density of the opacity, the severity of the opacity, and the size of the opacity. Such degrees of opacity may be represented, for example, by display colors, display densities, display patterns, or like display parameters.

When rendering is applied to the entire crystalline lens region in the three dimensional reconstructed image, a part of the rendered image corresponding to the entire crystalline lens region may be extracted and displayed. The process of extracting a part of a rendered image may be performed by means of, for example, the same or similar segmentation process as or to that performed by the segmentation processor 83.

Further, rendering may be applied to a part (partial region) of the crystalline lens region in the three dimensional reconstructed image. In this case, the segmentation processor 83 may be configured to apply the first segmentation to the three dimensional reconstructed image to identify a crystalline lens region therein, and then further apply the second segmentation to this crystalline lens region to identify a partial region thereof. In some alternative examples, the segmentation processor 83 may be configured to apply segmentation to the three dimensional reconstructed image to identify a partial region of a crystalline lens region therein.

The segmentation processor 83 of some examples may be configured to identify a partial region of a crystalline lens in the depth direction (Z direction, axial direction) of the subject's eye E (this partial region has a dimension (an extent) in the depth direction), from the crystalline lens region (or from the three dimensional reconstructed image). This partial region may be any of the following regions, for example: a nucleus region; the anterior region of the nucleus; the posterior region of the nucleus; a capsule region; a region shallower than a predetermined depth position; a region deeper than a predetermined depth position; a region located between the first depth position and the second depth position; and other partial regions. The rendering processor 81 may apply rendering to the partial region identified by the segmentation processor 83. This makes it possible to provide a distribution of opacities in this partial region. For example, a distribution of opacities in a depth range desired by the user can be provided.

The segmentation processor 83 may be configured to identify a partial region of the crystalline lens in a direction perpendicular to the depth direction (Z direction, axial direction) of the subject's eye E (this partial region has a dimension (an extent) in a direction perpendicular to the depth direction), from the crystalline lens region (or the three dimensional reconstructed image). Here, the direction perpendicular to the depth direction is, for example, the X direction, the Y direction, or the XY direction. For example, the segmentation processor 83 may partition the crystalline lens region into a plurality of sectors (segments) at equal angles and then obtain the state or condition of opacity, such as a distribution, amount, ratio, degree, etc., for each of the sectors.

When at least one of the nucleus region and the capsule region of the crystalline lens is identified by segmentation, the segmentation processor 83 may perform identification of a partial region of the crystalline lens based on the region identified. For example, when the nucleus region of the crystalline lens is identified, the segmentation processor 83 may identify the partial region using the contour of this nucleus region as a reference. More specifically, the partial region may be determined by enlarging or reducing the nucleus region by a predetermined size or dimension. When the capsule region of the crystalline lens is identified, the partial region may be determined in accordance with the shape (curved surface shape) of the capsule region. For example, a partial region having the front surface that is the same or similar curved surface as or to the anterior capsule region may be determined.

<Output Unit 9>

The output unit 9 outputs information from the slit lamp microscope 1. In some typical examples, the output unit 9 includes either one or both of a communication device and a display device. The communication device performs data communication between the slit lamp microscope 1 and other apparatuses. The display device displays information. The output unit 9 may include a recording device (e.g., data writer, drive device) forwriting (recording) information on a recording medium, a printer for recording (printing) information on a printing medium, or like devices.

The communication device included in the output unit 9 performs data communication between the slit lamp microscope 1 and another apparatus. In other words, the communication device performs transmission of data to another apparatus and reception of data transmitted from another apparatus. The system or method of the data communication executed by the communication device may be selected accordingly. For example, the communication device may include any one or more of various kinds of communication interfaces such as a communication interface conforming to the Internet, a communication interface conforming to a dedicated line, a communication interface conforming to a local area network (LAN), and a communication interface conforming to near field communication. The data communication may include any one or both of wireless communication and wired communication. Data sent and received by the communication device may be encrypted. If this is the case, for example, any one or both of the controller 7 and the data processor 8 include(s) at least one of an encryptor and a decryptor. The encryptor is configured to encrypt data to be sent by the communication device. The decryptor is configured to decrypt data having been received by the communication device.

The display device included in the output unit 9 is configured to display various kinds of information under the control of the controller 7. The display device may include a flat panel display such as a liquid crystal display (LCD). Note that the display device may be a peripheral device of the slit lamp microscope 1.

<Other Elements>

In addition to the elements shown in FIG. 1, the slit lamp microscope 1 may further include an operation device. In some other aspect examples, an operation device may be a peripheral device of the slit lamp microscope 1. The operation device includes a device for operating the slit lamp microscope 1 and/or a device for inputting information. The operation device includes, for example, a button, a switch, a lever, a dial, a handle, a knob, a mouse, a keyboard, a trackball, an operation panel, or the like. A device such as a touch screen may be employed in which a display device and an operation device are integrated (combined). The subject (patient) or an assistant may operate the slit lamp microscope 1 by using the display device and the operation device.

<Alignment>

A description will be given of the alignment of the slit lamp microscope 1 with respect to the subject's eye E. Alignment, in general, is an operation to place an optical system of an apparatus at an appropriate position for photography or measurement of the subject's eye E. The alignment of the present aspect example is an operation to place the illumination system 2 and the photography system 3 at appropriate positions for acquisition of a moving image (a plurality of anterior segment images) as shown in FIG. 3.

There are various kinds of techniques for alignment of an ophthalmic apparatus. While some alignment techniques will be described below, alignment techniques applicable to the present aspect example are not limited to them.

One of the alignment techniques applicable to the present aspect example is stereo alignment. Stereo alignment may be applicable to an ophthalmic apparatus capable of photographing an anterior segment from two or more mutually different directions (two or more mutually different viewpoints). A specific method of stereo alignment is disclosed by the present applicant in Japanese Unexamined Patent Application Publication No. 2013-248376. Stereo alignment includes, for example, the following steps: a step of photographing the anterior segment from different directions by two or more anterior segment cameras to acquire two or more photographed images; a step of analyzing the photographed images by a processor to determine a three dimensional position of the subject's eye; and a step of performing movement control of an optical system by a processor based on the three dimensional position determined. With such an alignment operation, the optical system (the illumination system 2 and the photography system 3 in the present example) is brought to and placed at an appropriate alignment position with respect to the subject's eye. The position of the pupil (e.g., the center of the pupil or the center of gravity of the pupil) of the subject's eye is used as a reference (or an indicator) in a typical stereo alignment.

In addition to the stereo alignment described hereinbefore, any known alignment techniques may be employed, such as an alignment technique using a Purkinje image formed by alignment light, an alignment technique using an optical lever, or an alignment technique using an alignment indicator. The alignment technique using a Purkinje image and the alignment technique using an optical lever or an alignment indicator uses the position of the corneal apex of the subject's eye as a reference.

Conventional and typical alignment techniques including the above examples are performed for the purpose of matching the optical axis of an optical system with the axis of a subject's eye. On the other hand, the present aspect example may perform alignment so as to place the illumination system 2 and the photography system 3 at a position corresponding to the scan start position.

The first example of the alignment of the present aspect example may be carried out in the following manner. First, alignment by referring to the pupil or corneal apex of the subject's eye E may be performed by applying any of the alignment techniques described above. Then, the illumination system 2 and the photography system 3 may be moved (in the X direction) by a distance corresponding to a standard value of the corneal radius determined in advance. Note that a measurement value of the corneal radius of the subject's eye E may be used instead of the standard value.

The second example of the alignment of the present aspect example may be carried out in the following manner. First, alignment by referring to the pupil or corneal apex of the subject's eye E may be performed by applying any of the alignment techniques described above. Second, the corneal radius of the subject's eye E may be measured by analyzing an image of anterior segment. Third, the illumination system 2 and the photography system 3 may be moved (in the X direction) by a distance corresponding to the measurement value of the corneal radius of the subject's eye E. The image of the anterior segment analyzed in the present example is an anterior segment image obtained by the photography system 3 or another image, for example. This another image here may be an image of any kind, such as an image obtained by an anterior segment camera, an image obtained by an anterior segment OCT, or the like.

The third example of the alignment of the present aspect example may be carried out in the following manner. First, the first edge position of the cornea may be determined by analyzing an image of the anterior segment acquired by the anterior segment camera for stereo alignment or by the photography system 3. Then, the illumination system 2 and the photography system 3 may be moved to a position corresponding to the first edge position by applying stereo alignment.

It should be noted that alignment may be performed by referring to the pupil or corneal apex of the subject's eye E by applying any of the alignment techniques described above, and then the anterior segment scan with slit light may be started from the position determined by the alignment. In such a case as well, a scan sequence may be determined to scan the entire cornea C. For example, the scan sequence may be determined such that the scan is performed to the left from the position determined by the alignment and then to the right.

<Some Additional Matters and Items>

The slit lamp microscope 1 may be provided with a fixation system configured to output light for fixation of the subject's eye E (referred to as fixation light). The fixation system of some typical examples includes at least one visible light source (referred to as a fixation light source(s)) or a display device configured to display an image such as a landscape chart or a fixation target. The fixation system of some example aspects is arranged coaxially or non-coaxially with the illumination system 2 or the photography system 3. The fixation system may include an internal fixation system and/or an external fixation system. The internal fixation system is configured to present a fixation target to the subject through the optical path of an optical system of an apparatus. The external fixation system is configured to present a fixation target to the subject from outside the optical path of an optical system of an apparatus.

The types (kinds) of images that may be acquired by the slit lamp microscope 1 are not limited to the moving image of the anterior segment (that is, the plurality of anterior segment images) described above. For example, the slit lamp microscope 1 may acquire any of the following types of images: a three dimensional image constructed based on the moving image; a rendered image constructed based on the three dimensional image; a transillumination image; a moving image representing movement of a contact lens applied to the subject's eye; and an image representing a gap between a contact lens and the corneal surface by fluorescent agent administration. The slit lamp microscope 1 of some examples may be capable of carrying out fundus photography, corneal endothelial cell photography, Meibomian gland photography, or other modalities. In the case where the slit lamp microscope 1 is capable of acquiring a transillumination image, the slit lamp microscope 1 may perform any of the following processes, for example: the process of displaying the above-mentioned rendered image and the transillumination image; the process of executing image synthesis (image composition) of the rendered image and the transillumination image; the process of applying image processing to one of the rendered image and the transillumination image based on the other; and the process of analyzing one of the rendered image and the transillumination image based on the other.

\<Operation\>

Figure 5:
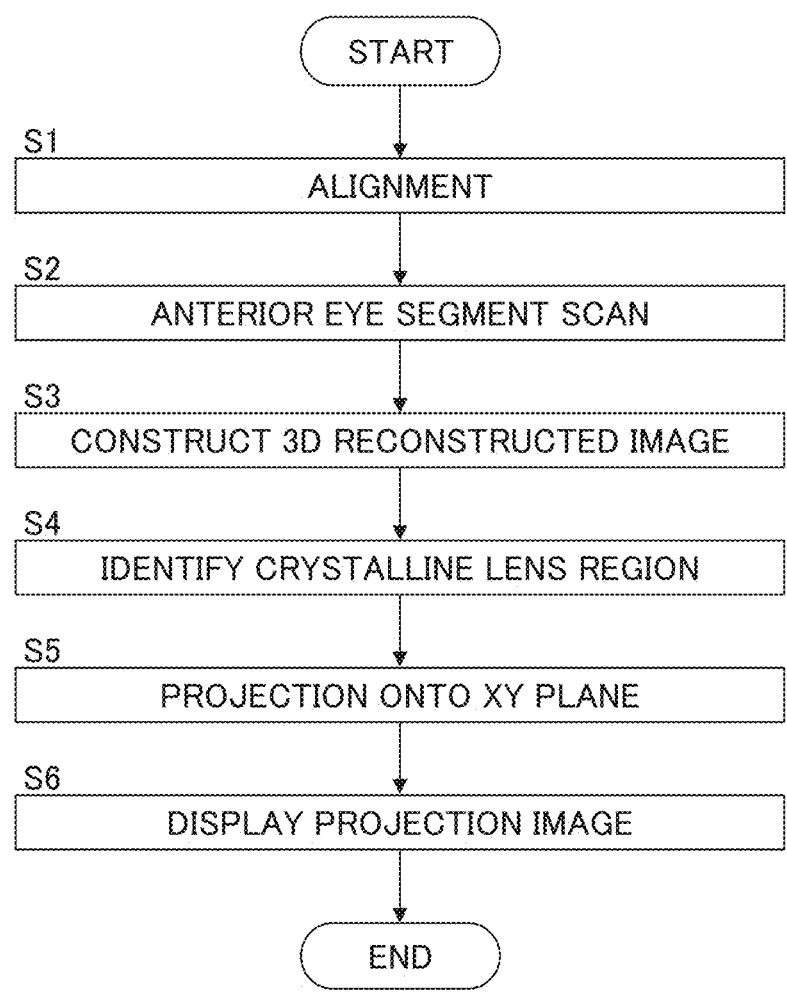
FIG. 5 is a flowchart illustrating the operation of the slit lamp microscope of the aspect example.

A description will be given of an operation of the slit lamp microscope 1. FIG. 5 shows an example of the operation.

While not shown in the drawings, the user (a subject, an examiner, or an assistant) inputs subject information into the slit lamp microscope 1 at any stage. The subject information that has been input is stored in the controller 7. The subject information of some typical examples includes identification information of the subject (referred to as subject ID).

Furthermore, background information may also be input. The background information is any kind of information related to the subject, and examples thereof include information acquired by a medical interview of the subject, information on a sheet filled in by the subject, information recorded in the electronic medical record of the subject, and the like. In some typical examples, the background information includes the subject's data on items such as gender, age, height, weight, disease name, possible disease name, examination result (e.g., visual acuity value, eye refractive power value, intraocular pressure value), history of a wearing device for refractive correction (e.g., history of wearing glasses, contact lenses) and the power of the device, examination history, and treatment history. These are merely examples, and possible items of the background information are not limited to them.

Further, in preparation for photography, the table on which the slit lamp microscope 1 is installed, the chair on which the subject sits, and the chin rest of the slit lamp microscope 1 are adjusted (all not shown in the drawings). For example, the heights of the table, chair, and chin rest are adjusted. The chin rest is provided with a chin rest member and a forehead rest member for stably positioning the face of the subject.

After the completion of the preparation, the subject sits on the chair, puts his/her chin on the chin rest member, and puts his/her forehead on the forehead rest member. Before or after these actions, the user performs an operation of issuing an instruction to start photography of the subject's eye. This operation may be conducted, for example, by pressing a photography start trigger button (not shown in the drawings) or inputting a voice instruction. Alternatively, the controller 7 may detect the completion of the preparation phase and automatically shift to the photography phase. In addition, a fixation target (not shown in the drawings) may be presented to the subject (the subject's eye E or the fellow eye thereof).

(S1: Alignment)

Upon commencing photography, the slit lamp microscope 1 performs alignment of the illumination system 2 and the photography system 3 with respect to the subject's eye E. Unlike general alignment operations for aligning the optical axis of an optical system with the corneal apex or the center of the pupil of the subject's eye E, the alignment in the step S1 is performed to place the illumination system 2 and the photography system 3 at a start position of the anterior segment scan to be performed in the step S2.

The mode (aspect) of the alignment of the step S1 may be freely selected, and may be any of the following modes, for example: stereo alignment; manual or automatic alignment using a Purkinje image; manual or automatic alignment using an optical lever; and manual or automatic alignment using an alignment index (alignment target).

Some aspect examples employ such conventional alignment techniques to perform alignment targeting the corneal apex or the center of the pupil. In addition, the controller 7 moves the illumination system 2 and the photography system 3, which have been moved by the alignment targeting the corneal apex or the center of the pupil, further to the scan start position (the position corresponding thereto).

Some other aspect examples perform alignment targeting the scan start position from the beginning. This alignment may include, for example, a process of identifying the scan start position by analyzing an image of the anterior eye segment, and a process of moving the illumination system 2 and the photography system 3 to a position corresponding to the identified scan start position. Here, the image of the anterior eye segment to be analyzed is, for example, an image captured from the front or an oblique direction, and the scan start position to be identified is, for example, the first edge position of the cornea described above or a position that is a predetermined distance away from the first edge position in the direction opposite to the axis of the subject's eye E.

A predetermined operation may be performed any of before, during, and after alignment. Examples of this operation include adjustment of illumination light amount (adjustment of the intensity of slit light), adjustment of the slit (adjustment of the width of the slit, adjustment of the length of the slit, adjustment of the orientation of the slit, etc.), adjustment of the image sensor 5 (sensitivity adjustment, gain adjustment, etc.), focus adjustment, or the like.

(S2: Scan Anterior Eye Segment)

The slit lamp microscope 1 scans the anterior segment of the subject's eye E by combining the projection of the slit light performed by the illumination system 2, the moving image photography performed by the photography system 3, and the movement of the illumination system 2 and the photography system 3 performed by the movement mechanism 6 in the manner described above.

Figure 6:
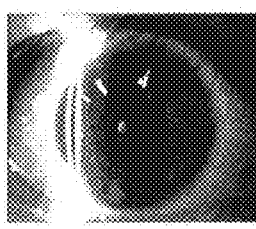
FIG. 6 is a diagram for describing the operation of the slit lamp microscope of the aspect example.
Figure 6:
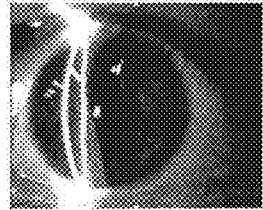
Figure 6:
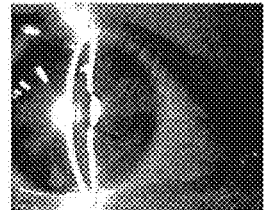
Figure 6:
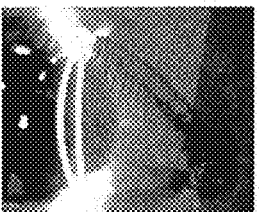

FIG. 6 shows several images, which represent an aspect of actually-performed anterior segment scanning, obtained by means of continuous photographing from the front. A person having ordinary skill in the art should understand, from these images, the aspect or state of the movement of the slit light being projected onto the anterior segment.

As a result of a single scan (that is, a scan from the scan start position to the scan end position), the image group (the plurality of anterior segment images) F1 to FN shown in FIG. 3 is obtained, for example.

The data processor 8 may be configured to perform predetermined processing on an image obtained by the scan application. For example, freely selected signal processing and/or freely selected image processing may be applied to an image obtained by the scan application, such as noise elimination, contrast adjustment, brightness adjustment, and color correction.

(S3: Construct Three Dimensional Reconstructed Image)

The reconstruction processor 82 applies three dimensional reconstruction to the plurality of anterior segment images collected in the step S2. This generates a three dimensional reconstructed image.

(S4: Identify Crystalline Lens Region)

The segmentation processor 83 applies segmentation to the three dimensional reconstructed image constructed in the step S3, thereby identifying a crystalline lens region.

Note that the segmentation processor 83 may apply further segmentation to the crystalline lens region, thereby identifying an image region corresponding to a predetermined partial region of the crystalline lens.

(S5: Projection onto XY Plane)

The crystalline lens region identified in the step S4 is a three dimensional image defined by the XYZ coordinate system. The rendering processor 81 applies projection onto the XY plane, to the crystalline lens region. This projection generates a projection image representing the opacity state in the crystalline lens. This projection image is similar to a transillumination image.

(S6: Display Projection Image)

The controller 7 displays the projection image constructed in the step S5 on the display device of the output unit 9.

As described above, the controller 7 may display information obtained from the plurality of anterior segment images and/or the three dimensional reconstructed images, together with the projection image. Examples of this information obtained from the plurality of anterior segment images and/or the three dimensional reconstructed images include depth information of opaque areas and information indicating the degree of opacity.

Here, an opaque area is identified, for example, by applying segmentation to the crystalline lens region (or, to the three dimensional reconstructed image or the plurality of anterior segment images). In some examples, the projection image and/or another rendered image may be used to identify an opaque area. Some examples may be operated to apply segmentation to the projection image to obtain an XY distribution of opaque areas, and analyze the crystalline lens region (or, the three dimensional reconstructed image or the plurality of anterior segment images) by referring to this XY distribution to generate a three dimensional distribution of the opaque areas.

Further, the controller 7 may control the communication device of the output unit 9 to transmit information to another apparatus. Examples of this information transmitted include the plurality of anterior segment images, the three dimensional reconstructed image, the projection image, and other kinds of information.

Examples of an apparatus to which the information is transmitted include an information processing apparatus and a storage. The information processing apparatus is, for example, a server on a wide area network, a server on a LAN, a computer terminal, or the like. The storage may be a storage device provided on a wide area network, a storage provided on a LAN, or the like.

Examples of the information displayed and/or transmitted may include the background information described above. In some alternative examples, the background information may be supplementary information attached to an image. In general, the data structure of the information displayed and/or transmitted may be selected accordingly.

In some typical examples, the information displayed and/or transmitted may include an image of the subject's right eye and an image of the subject's left eye. The image of the right eye and the image of the left eye can be obtained by applying the operations performed by the present example to the right eye and the left eye, respectively. The subject's eye information described above is attached to each of the image of the right eye and the image of the left eye. The image of the right eye and the image of the left eye can be distinguished from each other by referring to the attached subject's eye information.

Identification information of the subject is transmitted together with the image acquired by the slit lamp microscope 1. The identification information may be the subject ID input to the slit lamp microscope 1, or identification information generated based on the subject ID. For example, the subject ID used for personal identification in the facility where the slit lamp microscope 1 is installed (referred to as internal identification information) may be converted into external identification information used outside the facility. Such identification information conversion makes it possible to improve the information security of personal information such as images and background information.

This ends the description of the operations of the present example.

<Effects>

Some advantageous effects achieved by the slit lamp microscope 1 of the present aspect example will be described.

The slit lamp microscope 1 of the present aspect example includes a scanner (the illumination system 2, the photography system 3, and the movement mechanism 6) and the rendering processor 81. The scanner is configured to scan the anterior segment of the subject's eye E with slit light, thereby collecting the plurality of cross sectional images F1 to FN. The rendering processor 81 is configured to apply rendering to a three dimensional image created from the plurality of cross sectional images collected by the scanner. This three dimensional image to which the rendering is applied is, for example, an entire three dimensional reconstructed image of the plurality of cross sectional images collected by the scanner, or part of a three dimensional reconstructed image of the plurality of cross sectional images collected by the scanner.

In place of diaphanoscopy that depicts opaque areas in the crystalline lens as shadows of a light beam reverting from the retina, the slit lamp microscope 1 of the present aspect example is capable of conducting a novel observation technique that depicts opaque areas from a group of cross sectional images obtained by scanning the anterior segment with the slit light. Therefore, the slit lamp microscope 1 of the present aspect example is capable of adjusting the amount of illumination light (and imaging sensitivity). This makes it possible to perform management of the brightness of images and management of image quality.

Due to such an advantage, it becomes possible to use images obtained by the slit lamp microscope 1 of the present aspect example for quantitative diagnosis. For example, it becomes possible to use the images for objective evaluation of the grade of cataract in addition to subjective evaluation. Further, it becomes possible to apply automatic image analysis using an analysis program and/or machine learning to images obtained by the slit lamp microscope 1 of the present aspect example.

In addition, the slit lamp microscope 1 of the present aspect example can provide a three dimensional distribution of opaque areas of the crystalline lens, unlike diaphanoscopy that can only provide a two dimensional distribution of opaque areas of the crystalline lens.

As a result, the slit lamp microscope 1 of the present aspect example can provide a novel ophthalmic observation technique in which the drawbacks of diaphanoscopy are eliminated.

In the present aspect example, the rendering processor 81 may be configured to apply projection onto a predetermined plane, to the three dimensional image created from the plurality of cross sectional images collected by the scanner. Here, the predetermined plane may be determined to be a plane perpendicular to the depth direction (Z direction, axial direction) of the subject's eye E (the predetermined plane may be the XY plane). This configuration may be used for construction of a planar image (two dimensional image) similar to a transillumination image, for example.

The slit lamp microscope 1 of the present aspect example may further include the reconstruction processor 82 and the segmentation processor 83. The reconstruction processor 82 is configured to apply three dimensional reconstruction to the plurality of cross sectional images collected by the scanner. The segmentation processor 83 is configured to apply segmentation to a three dimensional reconstructed image constructed by the reconstruction processor 82. The three dimensional reconstructed image is used for setting the three dimensional image to which the rendering is applied by the rendering processor 81.

According to this configuration, the rendering can be applied to a desired part of the region scanned with the slit light.

In the present aspect example, the segmentation processor 83 may be configured to identify a crystalline lens region from the three dimensional reconstructed image constructed by the reconstruction processor 82. If this is the case, the three dimensional image to which the rendering is applied by the rendering processor 81 includes at least part of the crystalline lens region identified by the segmentation processor 83. This configuration can be used for construction of a planar image (two dimensional image) similar to a transillumination image, for example.

In the present aspect example, the rendering processor 81 may be configured to apply the rendering to the crystalline lens region identified by the segmentation processor 83.

According to this configuration, it becomes possible to construct a rendered image for the entire region of the crystalline lens imaged by scanning using the slit light.

In the present aspect example, the segmentation processor 83 is configured to apply further segmentation to the crystalline lens region identified from the three dimensional reconstructed image constructed by the reconstruction processor 82, thereby identifying a partial region that has a dimension or an extent in the depth direction (Z direction, axial direction) of the subject's eye E. Further, the rendering processor 81 may be configured to apply the rendering to this partial region of the crystalline lens region.

According to this configuration, a rendered image of a part of the crystalline lens region can be constructed. For example, it becomes possible to construct a rendered image of a desired part of the crystalline lens region.

In the present aspect example, the segmentation processor 83 may be configured to identify at least one region of a capsule region and a nucleus region from the crystalline lens region identified from the three dimensional reconstructed image constructed by the reconstruction processor 82, and then identify the above-mentioned partial region based on the at least one region identified.

According to this configuration, main (major, chief, important) structures of the crystalline lens (capsule, nucleus) can be referred to in order to determine the partial region of the crystalline lens to which the rendering is applied by the rendering processor 81. This makes it possible to determine the region to which the rendering is applied in a suitable manner. For example, region determination may be performed on basis of the layer structure of the crystalline lens.

The slit lamp microscope 1 of the present aspect example makes it possible to implement scanning of anterior eye segment with slit light by means of the following configuration. That is, the scanner includes the illumination system 2, the photography system 3, and the movement mechanism 6. The illumination system 2 is configured to project the slit light onto the anterior segment of the subject's eye E. The photography system 3 is configured to perform photography of the anterior segment from a direction different from the illumination system 2. The movement mechanism 6 is configured to move the illumination system 2 and the photography system 3. The photography system 3 performs repetitive photography (repetitive acquisition of images) in parallel with movement of the illumination system 2 and the photography system 3 performed by the movement mechanism 6. This repetitive photography is, for example, moving image photography at a photographing rate set in advance.

The movement mechanism 6 of the present aspect example may be configured to move the illumination system 2 and the photography system 3 in the X direction for anterior eye segment scanning with slit light. The movement mechanism 6 of the present aspect example may be capable of moving the illumination system 2 and the photography system 3 in a three dimensional manner for alignment.

Furthermore, the slit lamp microscope 1 of the present aspect example may have a function as a Scheimpflug camera, for example, in order to make it possible to photograph an area from the anterior surface of the cornea to the posterior surface of the crystalline lens by a single shot. For this purpose, the photography system 3 may include the optical system 4 and the image sensor 5. The optical system 4 is configured to direct light coming from the anterior eye segment onto which the slit light is projected. The image sensor 5 includes a light detecting plane and is configured to receive the light directed by the optical system 4. In addition, the slit lamp microscope 1 may be configured in such a manner that the subject plane along the optical axis of the illumination system 2, the optical system 4, and the image sensor 5 (the light detecting plane) satisfy the Scheimpflug condition.

Second Aspect Example

The present aspect example gives a description of an ophthalmic information processing apparatus. Any of the matters or items described in the first aspect example may be combined with or incorporated in the present aspect example.

Figure 7:
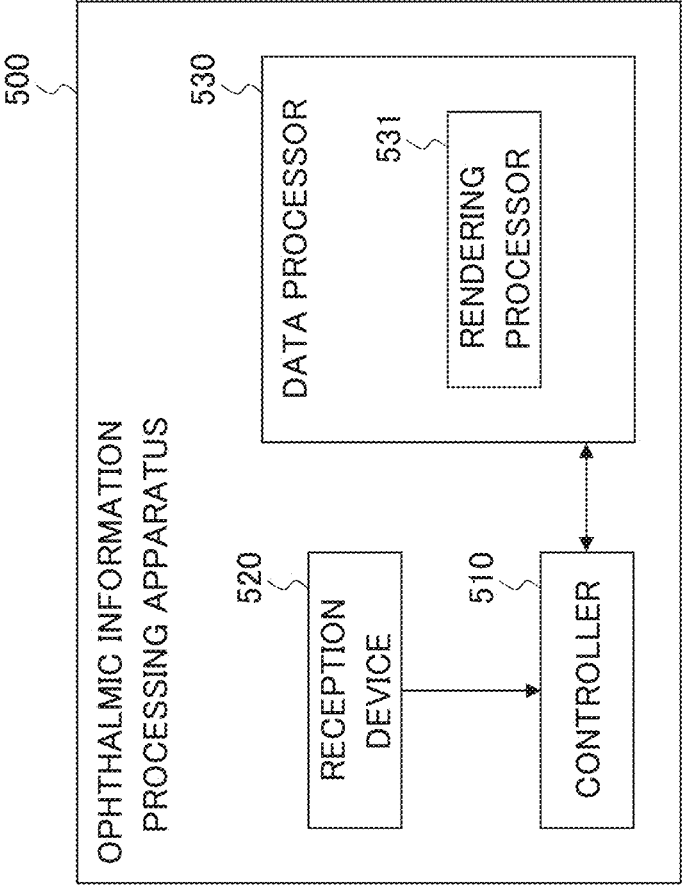
FIG. 7 is a schematic diagram illustrating the configuration of the ophthalmic information processing apparatus of the aspect example.

An example of the present aspect example is shown in FIG. 7. The ophthalmic information processing apparatus 500 includes the controller 510, the reception device 520, and the data processor 530. The controller 510 controls each part of the ophthalmic information processing apparatus 500.

The reception device 520 receives a plurality of cross sectional images collected by scanning an anterior segment of a subject's eye with slit light. The plurality of cross sectional images is obtained, for example, by an ophthalmic imaging apparatus having the same or similar configuration as or to the scanner of the slit lamp microscope 1 of the first aspect example. The reception device 520 receives the plurality of cross sectional images from the outside (for example, from an ophthalmic apparatus, an image archiving system, a recording medium, or other apparatuses or devices). The reception device 520 may include, for example, a communication device or a drive device.

The data processor 530 includes the rendering processor 531. The rendering processor 531 is configured to apply rendering to a three dimensional image created from the plurality of cross sectional images received by the reception device 520. The rendering processor 531 has, for example, the same or similar function and configuration as or to the rendering processor 81 of the first aspect example. The three dimensional image to which the rendering is applied may also be the same as that in the first aspect example.

Figure 8:
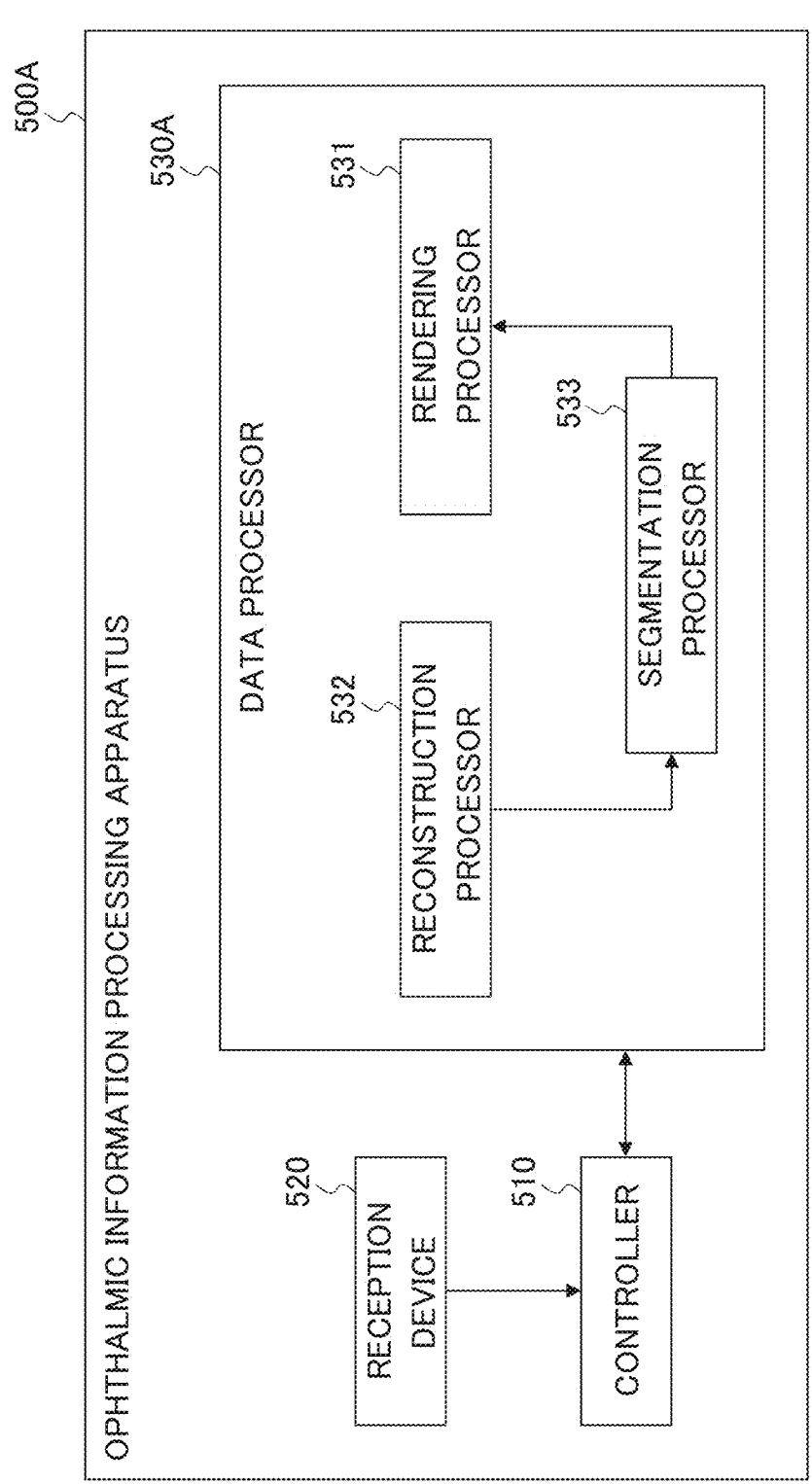
FIG. 8 is a schematic diagram illustrating the configuration of the ophthalmic information processing apparatus of the aspect example.

Another example of the present aspect example is shown in FIG. 8. The ophthalmic information processing apparatus 500A includes the controller 510, the reception device 520, and the data processor 530A. The controller 510 and the reception device 520 are the same as or similar to those in the example of FIG. 7.

The data processor 530A includes the reconstruction processor 532 and the segmentation processor 533, in addition to the rendering processor 531 same as or similar to the rendering processor 531 in the example of FIG. 7. The reconstruction processor 532 has, for example, the same or similar function and configuration as or to the reconstruction processor 82 in the first aspect example. The segmentation processor 533 has, for example, the same or similar function and configuration as or to the segmentation processor 83 in the first aspect example.

According to the ophthalmic information processing apparatus 500 (or 500A) of the present aspect example as described above, a novel ophthalmic observation technique without the drawbacks of diaphanoscopy can be provided by, for example, combining the ophthalmic information processing apparatus 500 (or 500A) with an ophthalmic imaging apparatus having the same or similar configuration as or to the scanner of the slit lamp microscope 1 of the first aspect example.

By combining or incorporating any of the matters or items described in the first aspect example with or in the present aspect example, an advantageous effect corresponding to the matters or items combined or incorporated can be achieved.

Third Aspect Example

The present aspect example gives a description of an ophthalmic system including an ophthalmic imaging apparatus, an information processing apparatus, and an image interpretation computer terminal. The ophthalmic imaging apparatus has at least a function as a slit lamp microscope (the function as the scanner of the first aspect example). A slit lamp microscope included in the ophthalmic imaging apparatus may be the slit lamp microscope of the first aspect example. Note that the ophthalmic imaging apparatus does not have to have a rendering processor. Below, a description will be given while referring accordingly to the elements, the configurations, and the reference characters of the first aspect example.

Figure 9:
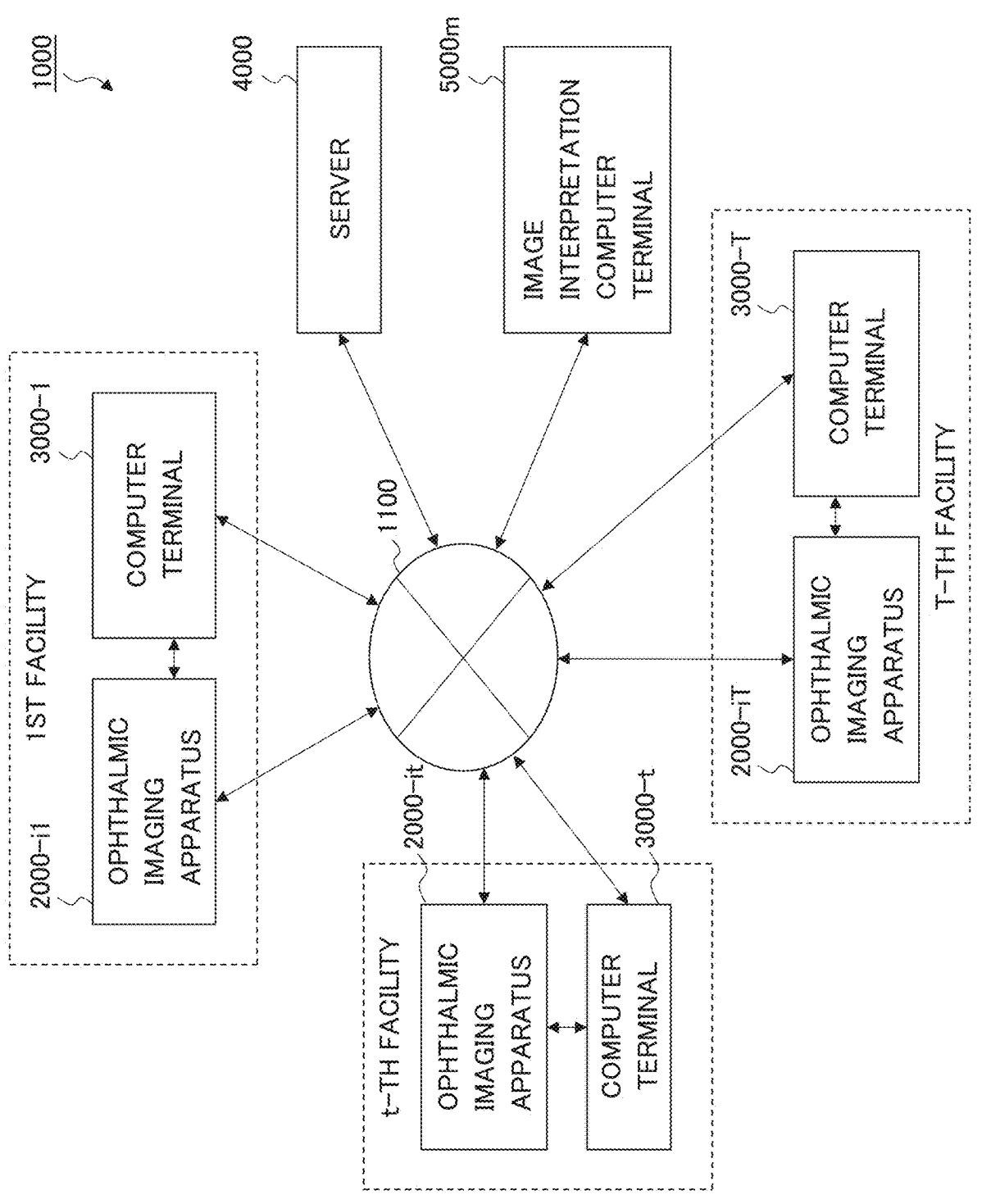
FIG. 9 is a schematic diagram illustrating the configuration of the ophthalmic system of the aspect example.

The ophthalmic system 1000 illustrated in FIG. 9 is configured using a communication channel (communication line) 1100 that is used for establishing connections between each of the number T of facilities (the first facility to the T-th facility) where ophthalmic imaging is conducted, the server 4000, and the image interpretation computer terminal 5000$m$.

Here, the ophthalmic imaging includes at least anterior segment photography using a slit lamp microscope. This anterior segment photography includes at least the anterior segment scanning with slit light described in the first aspect example.

Each of the facilities (t-th facility: where t=1 to T, T is any positive integer) is provided with the ophthalmic imaging apparatus 2000-$i_t$ (where $i_t$=1 to $K_t$, $K_t$ is any positive integer). In other words, one or more ophthalmic imaging apparatuses 2000-$i_t$ are installed in each of the facilities (t-th facility). The ophthalmic imaging apparatus 2000-$i_t$ constitutes a part of the ophthalmic system 1000. The ophthalmic system 1000 may include an examination apparatus that is capable of performing examination other than ophthalmic examination.

The ophthalmic imaging apparatus 2000-$i_t$ of the present example has the function of an "imaging apparatus" that performs imaging of eyes, and the function of a "computer" that performs various kinds of data processing and communicates with external devices. For another example, an imaging apparatus and a computer may be provided separately from each other. If this is the case, the imaging apparatus and the computer may communicate with each other. There may be any number of imaging apparatuses and any number of computers. For example, a single computer and a plurality of imaging apparatuses can be provided.

The "imaging apparatus" in the ophthalmic imaging apparatus 2000-$i_t$ includes at least a slit lamp microscope. This slit lamp microscope may be the slit lamp microscope of the first aspect example.

Each of the facilities (t-th facility) is provided with an information processing apparatus that can be used by an assistant or a subject (that is, the computer terminal 3000-$t$). The computer terminal 3000-$t$ is a computer for use in the corresponding facility. The computer terminal 3000-$t$ may be, for example, a mobile terminal such as a tablet terminal or a smartphone, or a server installed in the corresponding facility. The computer terminal 3000-$t$ may also include a wearable device such as a wireless earphone. Note that the computer terminal 3000-$t$ is only required to be a computer capable of realizing its functions in the corresponding facility. The computer terminal 3000-$t$ may be, for example, a computer placed outside the corresponding facility such as a cloud server.

The ophthalmic imaging apparatus 2000-$i_t$ and the computer terminal 3000-$t$ may communicate with each other through a network such as a network built in the t-th facility (e.g., in-house LAN), a wide area network (e.g., the Internet), or near-field communication technology.

The ophthalmic imaging apparatus 2000-$i_t$ may have the function as a communication device such as a server. If this is the case, the ophthalmic imaging apparatus 2000-$i_t$ and the computer terminal 3000-$t$ may communicate directly with each other. This makes it possible for the server 4000 and the computer terminal 3000-$t$ to communicate with each other via the ophthalmic imaging apparatus 2000-$i_t$. Therefore, the function of performing communication between the computer terminal 3000-$t$ and the server 4000 becomes omissible.

The server 4000 of some typical examples is installed in a facility different from any of the first to the t-th facilities, for example, in a management center. The server 4000 can communicate with the image interpretation computer terminal 5000$m$ (where m=1 to M, M is any positive integer) via a network. The network is, for example, a LAN or a wide area network. Further, the server 4000 can communicate with at least one of the ophthalmic imaging apparatuses 2000-$i_t$ installed in the first to the t-th facilities via a wide area network.

The server 4000 has the following functions, for example: the function of relaying communication between the ophthalmic imaging apparatus 2000-$i_t$ and the image interpretation computer terminal 5000$m$; the function of recording the contents of the communication; the function of storing data and information acquired by the ophthalmic imaging apparatus 2000-$i_t$; and the function of storing data and information acquired by the image interpretation computer terminal 5000$m$. In addition, the server 4000 may have a data processing function.

The image interpretation computer terminal 5000$m$ includes a computer that can be used for interpretation of images of a subject's eye (e.g., interpretation of a plurality of cross sectional images acquired through anterior segment scanning, or interpretation of a rendered image of a three dimensional image constructed based on the cross sectional images acquired through the anterior segment scanning) acquired by the ophthalmic imaging apparatus 2000-$i_t$, as well as that can be used for creation of reports. The image interpretation computer terminal 5000$m$ may have a function of data processing.

Figure 10:
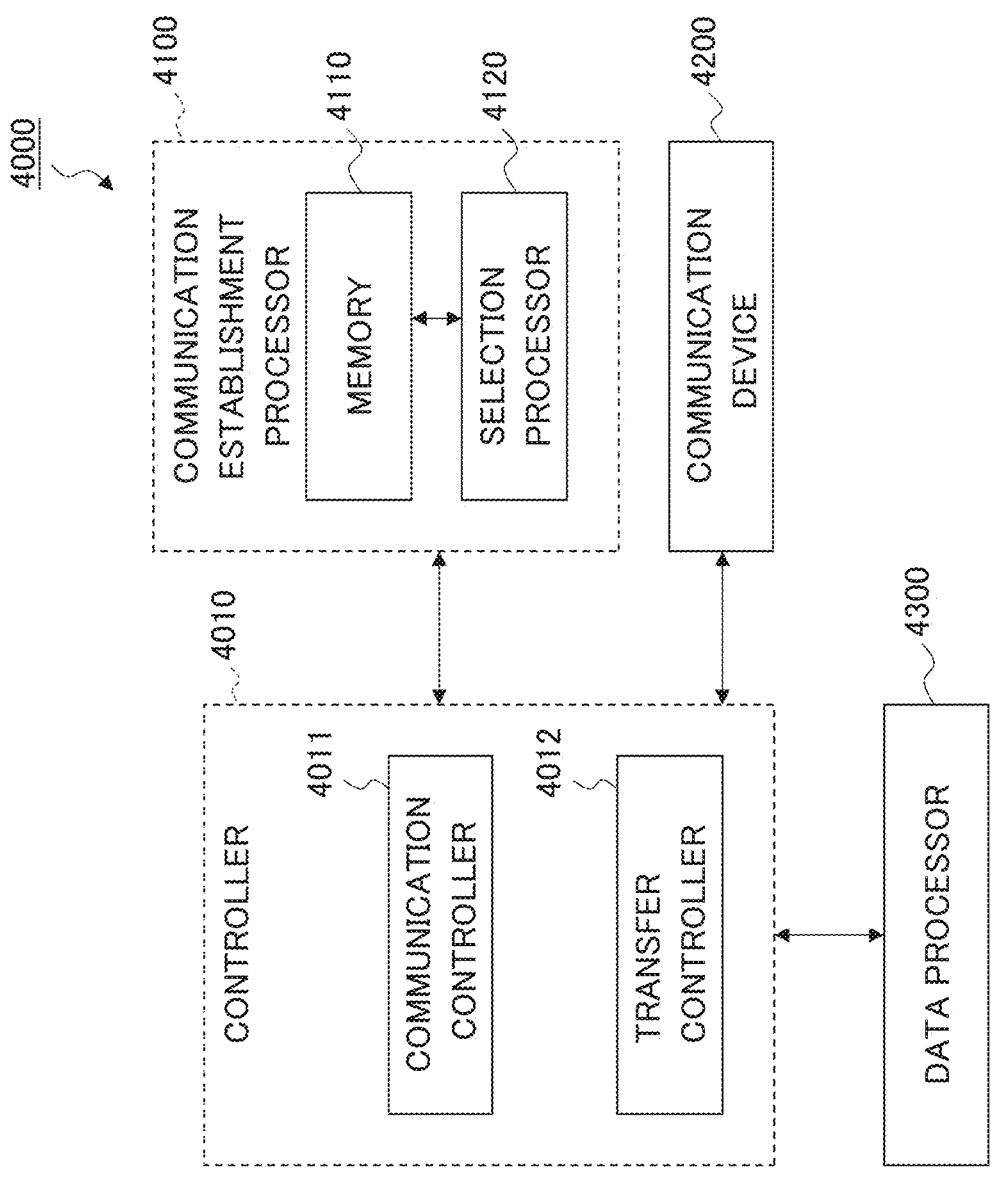
FIG. 10 is a schematic diagram illustrating the configuration of the ophthalmic system of the aspect example.

Now given is a description of the server 4000. The server 4000 illustrated in FIG. 10 includes the controller 4010, the communication establishment processor 4100, and the communication device 4200.

The controller 4010 executes control of each part of the server 4000. The controller 4010 may be capable of executing other processing such as arithmetic processing. The controller 4010 includes a processor. The controller 4010 may further include a RAM, a ROM, a hard disk drive, a solid state drive, etc.

The controller 4010 includes the communication controller 4011 and the transfer controller 4012.

The communication controller 4011 is configured to perform control relating to the establishment of communication between a plurality of apparatuses that includes a plurality of ophthalmic imaging apparatuses 2000-$i_t$, a plurality of computer terminals 3000-$t$, and a plurality of image interpretation computer terminals 5000$m$. For example, the communication controller 4011 may be configured to send a control signal for establishing communication to each of two or more apparatuses selected by the selection processor 4120 from among a plurality of apparatuses included in the ophthalmic system 1000. The selection processor 4120 will be described later.

The transfer controller 4012 is configured to perform control relating to exchange (transmission and reception) of information between two or more apparatuses between which communication has been established by the communication establishment processor 4100 (and the communication controller 4011). For example, the transfer controller 4012 may be configured to transfer information transmitted from one of the at least two apparatuses between which communication has been established by the communication establishment processor 4100 (and the communication controller 4011), to another apparatus.

As a specific example, in the case where communication between the ophthalmic imaging apparatus 2000-$i_t$ and the image interpretation computer terminal 5000$m$ has been established, the transfer controller 4012 can transfer information transmitted from the ophthalmic imaging apparatus 2000-$i_t$ to the image interpretation computer terminal

5000$m$. This information transmitted from the ophthalmic imaging apparatus 2000-$i_t$ may include a plurality of cross sectional images. Conversely, the transfer controller 4012 can transfer information transmitted from the image interpretation computer terminal 5000$m$ to the ophthalmic imaging apparatus 2000-$i_t$. This information transmitted from the image interpretation computer terminal 5000$m$ may include an instruction to the ophthalmic imaging apparatus 2000-$i_t$, an interpretation report, or the like.

The transfer controller 4012 may have a function of processing information received from another apparatus. If this is the case, the transfer controller 4012 can transmit at least one of the received information and information created using the processing function, to an apparatus that is a destination of transfer.

For example, the transfer controller 4012 may extract part of the information transmitted from an apparatus such as the ophthalmic imaging apparatus 2000-$i_t$, and transmit the extracted information to an apparatus such as the image interpretation computer terminal 5000$m$.

In some aspect examples, the server 4000 or another apparatus may be configured to analyze information transmitted from an apparatus such as the ophthalmic imaging apparatus 2000-$i_t$. This information to be analyzed may include a plurality of cross sectional images or information generated by processing the plurality of cross sectional images, for example. In addition, a result of this analysis of the information (and its original information) may be sent to an apparatus such as the image interpretation computer terminal 5000$m$. Some aspect examples may be configured to execute interpretation, using an artificial intelligence engine or the like, of the plurality of cross sectional images (or a three dimensional image constructed based on the plurality of images, or a rendered image of the three dimensional image) transmitted from the ophthalmic imaging apparatus 2000-$i_t$, and then transmit a result of this interpretation to the image interpretation computer terminal 5000$m$ together with the plurality of cross sectional images.

In the case where a plurality of cross sectional images has been transmitted from the ophthalmic imaging apparatus 2000-$i_t$, the ophthalmic system 1000 may be configured in such a manner that the server 4000 or another apparatus constructs a three dimensional image (e.g., a three dimensional reconstructed image such as stack data or volume data) from this plurality of cross sectional images, and that the transfer controller 4012 sends the constructed three dimensional image to the image interpretation computer terminal 5000$m$.

In the case where stack data has been transmitted from the ophthalmic imaging apparatus 2000-$i_t$, the ophthalmic system 1000 may be configured in such a manner that the server 4000 or another apparatus constructs volume data from this stack data, and that the transfer controller 4012 sends the constructed volume data to the image interpretation computer terminal 5000$m$.

Data processing executable by the server 4000 or another apparatus is not limited to the examples described above. Data processing executable by the server 4000 or another apparatus may include data processing of any kind. For example, the server 4000 or another apparatus may be capable of performing a process such as rendering of a three dimensional image, artifact elimination, distortion correction, measurement, or the like.

The communication establishment processor 4100 is configured to perform the process of establishing communication between at least two apparatuses that have been selected from among a plurality of apparatuses including the plurality of ophthalmic imaging apparatuses 2000-$i_t$, the plurality of computer terminals 3000-$t$, and the plurality of image interpretation computer terminals 5000$m$. In the present aspect example, "establishing communication" refers to a concept which includes, for example, at least one of the followings: (1) establishing unidirectional communication from a state in which communication is disconnected; (2) establishing bidirectional communication from a state in which communication is disconnected; (3) switching from a state in which only data reception is possible to a state in which both data reception and data transmission are possible; and (4) switching from a state in which only data transmission is possible to a state in which both data transmission and data reception are possible.

In addition, the communication establishment processor 4100 can perform the process of disconnecting the established communication. In the present aspect example, "disconnecting communication" refers to a concept which includes, for example, at least one of the followings: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which data transmission and data reception are possible to a state in which only data reception is possible; and (5) switching from a state in which data transmission and data reception are possible to a state in which only data transmission is possible.

Each of the ophthalmic imaging apparatus 2000-$i_t$, the computer terminal 3000-$t$, and the image interpretation computer terminal 5000$m$ can send at least one of the following communication requests to the server 4000: a communication request (a call request) for calling another apparatus or the user thereof; and a communication request (an interruption request) for interrupting communication between two other apparatuses. A call request is issued manually or automatically, and an interruption request is issued manually or automatically. The server 4000 (the communication device 4200 therein) receives a communication request transmitted from the ophthalmic imaging apparatus 2000-$i_t$, the computer terminal 3000-$t$, or the image interpretation computer terminal 5000$m$.

The communication establishment processor 4100 of the present aspect example may include the selection processor 4120. For example, based on a communication request sent from the ophthalmic imaging apparatus 2000-$i_t$, the computer terminal 3000-$t$, or the image interpretation computer terminal 5000$m$, the selection device 4120 selects one or more apparatuses other than the apparatus that has sent the communication request, from among the ophthalmic imaging apparatus 2000-$i_t$, the computer terminal 3000-$t$, and the image interpretation computer terminal 5000$m$.

A specific example of the processing executed by the selection processor 4120 will be described. When a communication request sent from the ophthalmic imaging apparatus 2000-$i_t$ or the computer terminal 3000-$t$ is received (e.g., when a request for interpretation of an image acquired by the ophthalmic imaging apparatus 2000-$i_t$ is received), the selection processor 4120 selects, for example, any apparatus from among the plurality of image interpretation computer terminals 5000$m$. The communication establishment processor 4100 establishes communication between the selected image interpretation computer terminal 5000$m$, and at least one of the ophthalmic imaging apparatus 2000-$i_t$ and the computer terminal 3000-$t$.

The apparatus selection in response to a communication request is performed, for example, based on a preset attribute. Examples of the attribute include types of examination (e.g., types of imaging modalities, types of images, types of diseases, types of possible diseases), degrees of expertise required, levels of skills required, and types of languages. In the present example, for example, the specialized field and the level of skill of the person who conducts image interpretation are referred to. In order to implement the processing of the present example, the communication establishment processor 4100 may include the memory 4110 in which attribute information prepared in advance is stored. This attribute information includes attributes of the image interpretation computer terminals 5000$m$ and/or attributes of users (doctors, optometrists) of the image interpretation computer terminals 5000$m$.

The identification of users may be carried out using user identifiers (user IDs) respectively assigned to users in advance. Further, the identification of the image interpretation computer terminals 5000$m$ may be carried out using, for example, apparatus identifiers or network addresses respectively assigned to apparatuses in advance. In a typical example, the attribute information includes attributes of each user such as the user's specialized field (e.g., the department, the specialized disease), the user's degree of expertise, the user's level of skills, or the types of languages the user is able to use.

When the selection processor 4120 refers to the attribute information, a communication request to be sent from the ophthalmic imaging apparatus 2000-$i_t$, the computer terminal 3000-$t$, or the image interpretation computer terminal 5000$m$ may include information related to attributes. For example, an interpretation request (diagnosis request) to be transmitted from the ophthalmic imaging apparatus 2000-$i_t$ may include any of the followings: (1) information indicating the type of an imaging modality; (2) information indicating the type of images; (3) information indicating the name of a disease or the name of a possible disease; (4) information indicating the degree of difficulty in interpretation; and (5) information indicating a language used by a user of the ophthalmic imaging apparatus 2000-$i_t$ and/or a language used by a user of the computer terminal 3000-$t$.

Upon receiving such an interpretation request, the selection processor 4120 may select one or more of the image interpretation computer terminals 5000$m$ based on this interpretation request and the attribute information stored in the memory 4110. In this selection processing, the selection processor 4120 may compare the information related to attributes included in the interpretation request with information recorded in the attribute information stored in the memory 4110. With this comparison, the selection processor 4120 selects, for example, the image interpretation computer terminal(s) 5000$m$ corresponding to a doctor(s) (or an optometrist(s)) who satisfies any of the following attributes: (1) a doctor who is specializing in a corresponding imaging modality; (2) a doctor who is specializing in a corresponding type of images; (3) a doctor who is specializing in a corresponding disease (or a corresponding possible disease); (4) a doctor who is capable of conducting interpretation of a corresponding level of difficulty; and (5) a doctor who is capable of using a corresponding language.

The correspondence between doctors or optometrists and the image interpretation computer terminals 5000$m$ may be made by, for example, referring to user IDs input, at the time of logging in, to the image interpretation computer terminals 5000$m$ (or to the ophthalmic system 1000).

The communication device 4200 is configured to perform data communication with another apparatus such as any of the ophthalmic imaging apparatus 2000-i_t, the computer terminal 3000-t, and the image interpretation computer terminal 5000m. The system or method of the data communication and encryption may be performed in the same manner as in the communication device provided in the ophthalmic imaging apparatus 2000-i_t (the communication device of the output unit 9 in the first aspect example).

The server 4000 includes the data processor 4300. The data processor 4300 is configured to execute various kinds of data processes. The data processor 4300 may be configured to process a plurality of cross sectional images or a three dimensional image acquired by the ophthalmic imaging apparatus 2000-i_t (in particular, a slit lamp microscope). The data processor 4300 includes a processor, a primary storage, a secondary storage, and the like. The secondary storage stores a data processing program or the like. The function of the data processor 4300 is implemented by cooperation of software such as the data processing program and hardware such as the processor.

The server 4000 may provide data obtained by the data processor 4300 to another apparatus. For example, in the case where the data processor 4300 constructs a three dimensional image from a plurality of cross sectional images acquired by the ophthalmic imaging apparatus 2000-i_t, the server 4000 can transmit the constructed three dimensional image to the image interpretation computer terminal 5000m by using the communication device 4200. In the case where the data processor 4300 applies the rendering to a three dimensional image constructed by the ophthalmic imaging apparatus 2000-i_t or the data processor 4300, the server 4000 can transmit the constructed rendered image to the image interpretation computer terminal 5000m by using the communication device 4200. In the case where the data processor 4300 applies a measuring process to one or more cross sectional images or a three dimensional image, the server 4000 can transmit the obtained measurement data to the image interpretation computer terminal 5000m by using the communication device 4200. In the case where the data processor 4300 applies the distortion correction to one or more cross sectional images or a three dimensional image, the server 4000 can transmit the corrected image to the image interpretation computer terminal 5000m by using the communication device 4200.

Figure 11:
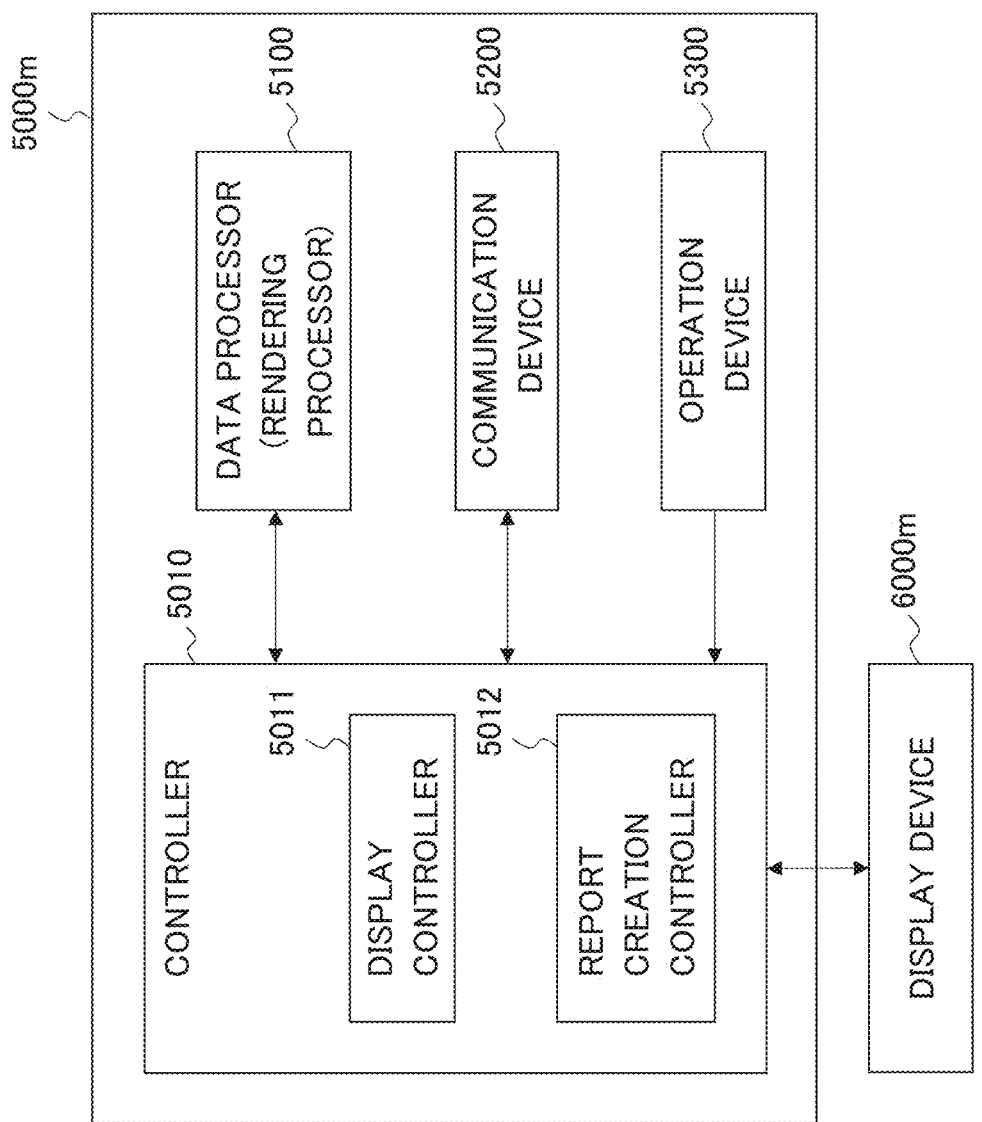
FIG. 11 is a schematic diagram illustrating the configuration of the ophthalmic system of the aspect example.

Next, a description is given of the image interpretation computer terminal 5000m. The image interpretation computer terminal 5000m illustrated in FIG. 11 includes the controller 5010, the data processor 5100, the communication device 5200, and the operation device 5300.

The data processor 5100 may have the same or similar function and configuration as or to the data processor 8 of the first aspect example. For example, the data processor 5100 may have at least the function and configuration of the rendering processor 81 of the first aspect example, and may further have the function and configuration of the reconstruction processor 82 and the function and configuration of the segmentation processor 83.

The controller 5010 executes control of each part of the image interpretation computer terminal 5000m. The controller 5010 may be capable of executing other processing such as arithmetic processing. The controller 5010 includes a processor, a RAM, a ROM, a hard disk drive, a solid state drive, etc.

The controller 5010 includes the display controller 5011. The display controller 5011 controls the display device 6000m. The display device 6000m may be included in the image interpretation computer terminal 5000m or may be a peripheral device connected to the image interpretation computer terminal 5000m. The display controller 5011 controls the display device 6000m to display an image of the anterior segment of the subject's eye E. For example, the display controller 5011 may control the display device 6000m to display a rendered image of a three dimensional image constructed based on a plurality of cross sectional images of the anterior segment of the subject's eye.

The controller 5010 includes the report creation controller 5012. The report creation controller 5012 executes various kinds of controls for creating a report regarding the information displayed by the display controller 5011. For example, the report creation controller 5012 controls the display device 6000m to display a screen and a graphical user interface (GUI) used for report creation. Further, the report creation controller 5012 inputs or records, into or on a predetermined report template, information input by the user, an image of the anterior segment, measurement data, analysis data, and the like.

The data processor 5100 executes various kinds of data processing. The data processor 5100 may be configured to process a plurality of cross sectional images or a three dimensional image acquired by the ophthalmic imaging apparatus 2000-i_t (in particular, a slit lamp microscope). Further, the data processor 5100 may be configured to process a three dimensional image or a rendered image constructed by another information processing apparatus such as the server 4000. The data processor 5100 includes a processor, a primary storage, a secondary storage, and the like. A data processing program or the like is stored in the secondary storage. The function of the data processor 5100 is implemented by cooperation of software such as the data processing program and hardware such as the processor.

The communication device 5200 performs data communication with another apparatus. This another apparatus is, for example, any of the ophthalmic imaging apparatus 2000-i_t, the computer terminal 3000-t, and the server 4000. The system of the data communication and encryption may be performed in the same manner as in the communication device of the ophthalmic imaging apparatus 2000-i_t.

The operation device 5300 is used to operate the image interpretation computer terminal 5000m and input information to the image interpretation computer terminal 5000m. In the present aspect example, the operation device 5300 is used to create a report. The operation device 5300 includes an operation device and an input device. The operation device 5300 includes, for example, a mouse, a keyboard, a trackball, an operation panel, a switch, a button, a dial, or the like. The operation device 5300 may include a touch screen.

The ophthalmic system 1000 of the present aspect example is capable of performing the following operations.

To begin with, the ophthalmic imaging apparatus 2000-i_t (a slit lamp microscope) performs scanning on the anterior segment of the subject's eye with slit light, thereby collecting a plurality of cross sectional images. The ophthalmic imaging apparatus 2000-i_t transmits the first transmission information including the collected plurality of cross sectional images to the server 4000 via the communication line 1100. Such an operation of the ophthalmic imaging apparatus 2000-i_t may be performed in the same manner as the operation of the first aspect example. In addition, the ophthalmic imaging apparatus 2000-i_t may be capable of performing any of the processes described in the first aspect example.

The server 4000 receives the first transmission information sent from the ophthalmic imaging apparatus 2000-i_t using the communication device 4200 (a reception device), and then stores the first transmission information in the memory 4110. Further, the server 4000 transmits, using the communication device 4200 (a transmission device), the second transmission information that includes at least the plurality of cross sectional images included in the first transmission information, to the image interpretation computer terminal 5000*m* via the communication line 1100.

The image interpretation computer terminal 5000*m* receives the second transmission information sent from the server 4000 using the communication device 5200 (a reception device). The user of the image interpretation computer terminal 5000*m* (the person who conducts image interpretation) performs interpretation based on the plurality of cross sectional images using a user interface (the operation device 5300, the display device 6000*m*, the report creation controller 5012, etc.). For example, the data processor 5100 applies rendering to a three dimensional image constructed based on the plurality of cross sectional images. A rendered image constructed by this rendering is displayed on the display device 6000*m* by the display controller 5011. The rendered image is, for example, a front image similar to a transillumination image. By conducting image interpretation of this front image, the user performs, for example, evaluation of the grade of cataract, and inputs a result of this evaluation to the image interpretation computer terminal 5000*m*. The image interpretation computer terminal 5000*m* transmits, using the communication device 5200 (a transmission device), the third transmission information that includes information (e.g., an image interpretation report) input using the user interface, to the server 4000 via the communication line 1100.

The server 4000 receives the third transmission information transmitted from the image interpretation computer terminal 5000*m* using the communication device 4200 (a reception device), associates the third transmission information with the first transmission information, and stores the third transmission information in the memory 4110.

As can be seen from the effects of the first aspect example, according to the ophthalmic system 1000 configured in this way, the user can appropriately conduct image interpretation based on the images of the anterior eye segment acquired in advance. The acquisition of the images of the anterior eye segment may be performed at a remote place. With a conventional technology, a doctor conducts a medical examination while operating a slit lamp microscope from a remote place, however, according to the present aspect example, a doctor only needs to conduct image interpretation based on images that have been acquired in advance. In other words, according to the present aspect example, a doctor can be made free from the time and effort required for conducting photography, which allows the doctor to concentrate on image interpretation. Therefore, the present aspect example contributes to expanding the area to which a high quality slit lamp microscope examination can be provided.

Fourth Aspect Example

The present aspect example gives a description of an ophthalmic system that includes an ophthalmic imaging apparatus, an information processing apparatus, and an image interpretation apparatus. The difference in configurations from the third aspect is that the image interpretation apparatus is provided instead of the image interpretation computer terminal. Note that the third aspect example and the fourth aspect example may be combined to configure an ophthalmic system that includes both an image interpretation computer terminal and an image interpretation apparatus. Below, a description will be provided while referring accordingly to the elements, the configurations, and the reference characters of any of the first, second, and third aspect examples.

Figure 12:
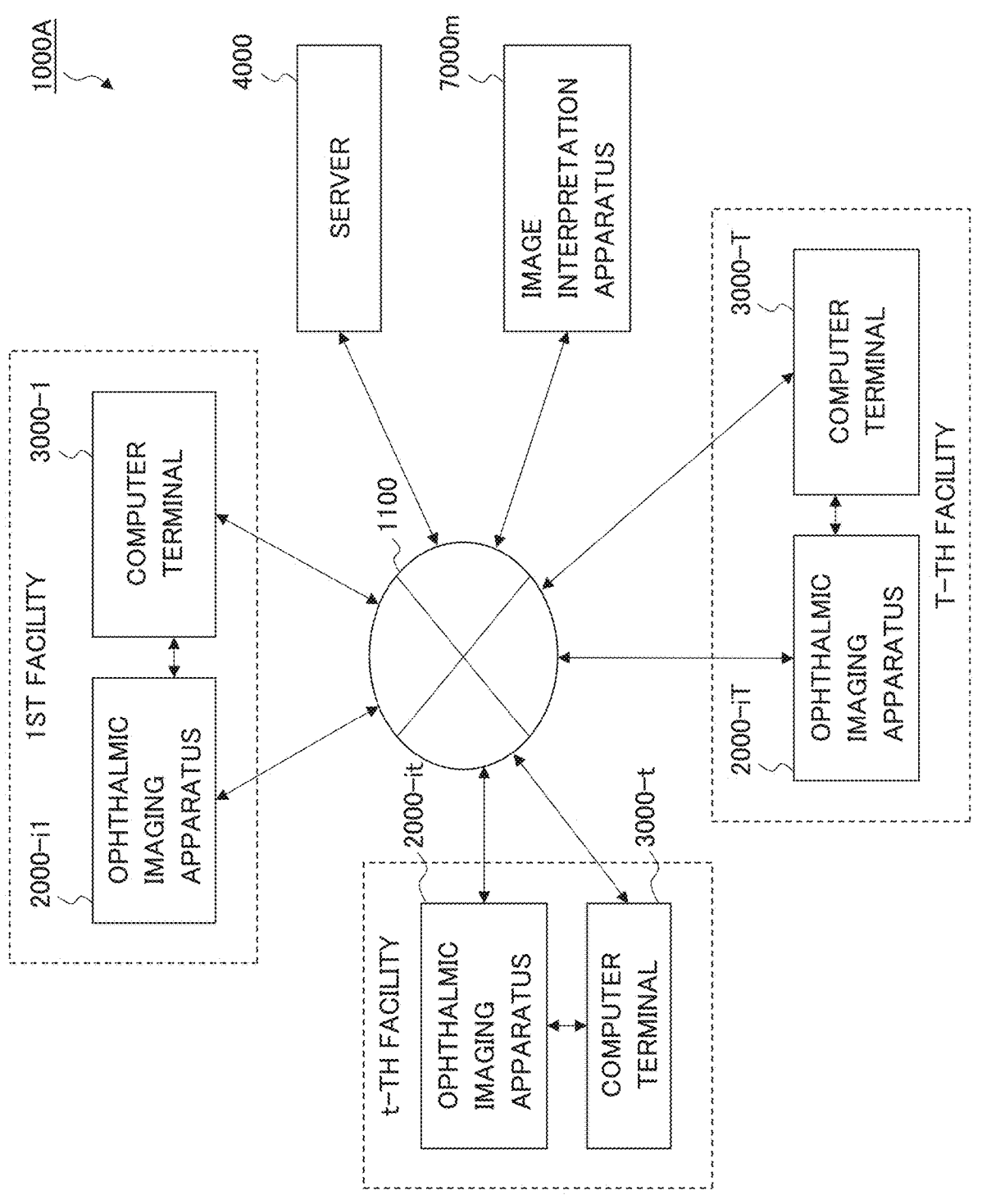
FIG. 12 is a schematic diagram illustrating the configuration of the ophthalmic system of the aspect example.

As mentioned above, the ophthalmic system 1000A illustrated in FIG. 12 has a configuration that includes the image interpretation apparatus 7000*m* in place of the image interpretation computer terminal 5000*m* of the ophthalmic system 1000 of the third aspect example. The image interpretation apparatus 7000*m* is a computer configured to execute interpretation of a plurality of cross sectional images acquired by the ophthalmic imaging apparatus 2000-$i_t$ (a slit lamp microscope) using an image processing processor and/or an artificial intelligence engine, for example.

Figure 13:
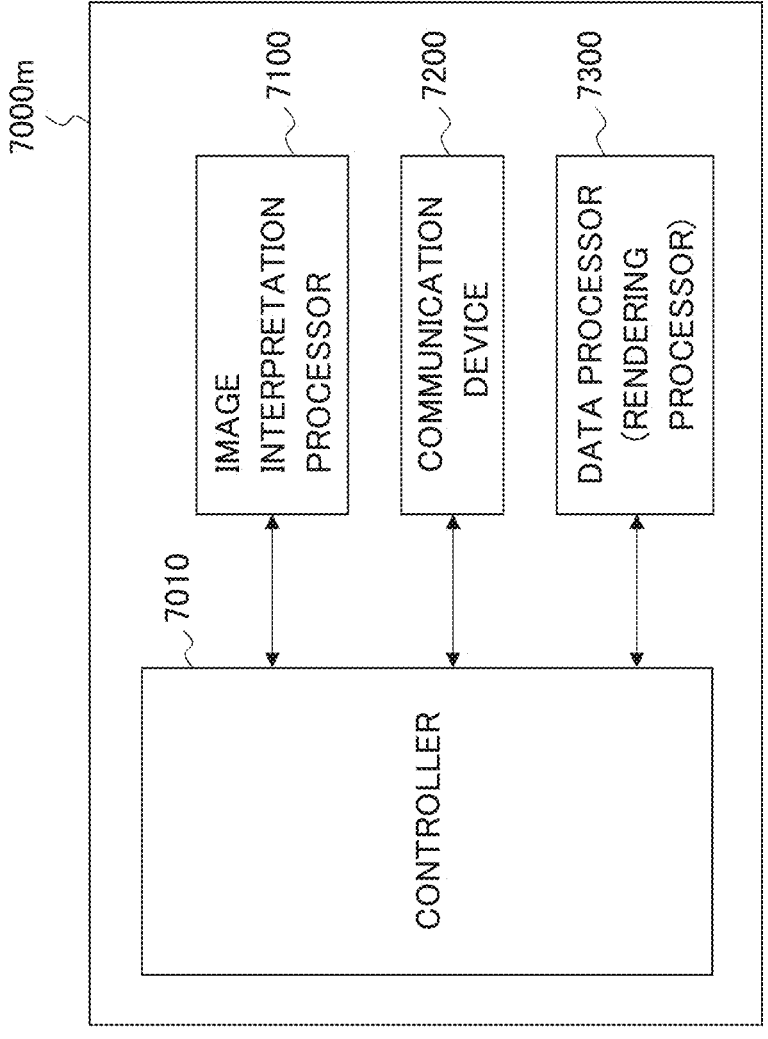
FIG. 13 is a schematic diagram illustrating the configuration of the ophthalmic system of the aspect example.

FIG. 13 shows a configuration example of the image interpretation apparatus 7000*m*. The image interpretation apparatus 7000*m* of the present example includes the image interpretation processor 7100, the communication device 7200, and the data processor 7300. The communication device 7200 is configured to perform data communication with other devices such as any of the ophthalmic imaging apparatus 2000-$i_t$, the computer terminal 3000-$t$, and the server 4000.

The data processor 7300 may have the same or similar function and configuration as or to the data processor 8 of the first aspect example. For example, the data processor 7300 may have at least the function and configuration of the rendering processor 81 of the first aspect example, and may further have the function and configuration of the reconstruction processor 82 and the function and configuration of the segmentation processor 83.

The image interpretation processor 7100 includes, for example, an image interpretation processor that operates in accordance with a program for image interpretation, and analyzes a plurality of cross sectional images (an image constructed based on the plurality of cross sectional images) to obtain findings. In some aspect examples, the image interpretation processor 7100 may include the artificial intelligence engine of the first aspect example, in order to obtain findings from a plurality of cross sectional images (an image constructed based on the plurality of cross sectional images). In the present aspect example, the data processor 7300 constructs a rendered image of a three dimensional image constructed based on a plurality of cross sectional images. Then, the image interpretation processor 7100 performs interpretation of this rendered image to obtain findings. In addition, the image interpretation processor 7100 may be configured to create a report based on findings obtained.

The ophthalmic system 1000A of the present aspect example is capable of performing the following operations.

To begin with, the ophthalmic imaging apparatus 2000-$i_t$ (a slit lamp microscope) performs scanning on the anterior segment of the subject's eye with slit light to collect a plurality of cross sectional images. The ophthalmic imaging apparatus 2000-$i_t$ transmits the first transmission information including the collected plurality of cross sectional images to the server 4000 via the communication line 1100. This operation of the ophthalmic imaging apparatus 2000-$i_t$ may be performed in the same manner as the operation of the above aspect examples. In addition, the ophthalmic imaging apparatus 2000-$i_t$ may be capable of performing any of the processes described in the above aspect examples.

The server 4000 receives the first transmission information sent from the ophthalmic imaging apparatus 2000-$i_t$ using the communication device 4200 (a reception device), and then stores the first transmission information in the memory 4110. Further, the server 4000 transmits, using the communication device 4200 (a transmission device), the second transmission information that includes at least the plurality of cross sectional images included in the first transmission information, to the image interpretation apparatus 7000*m* via the communication line 1100.

The image interpretation apparatus 7000*m* receives the second transmission information sent from the server 4000 using the communication device 7200 (a reception device). The image interpretation apparatus 7000*m* applies rendering to a three dimensional image constructed based on the plurality of cross sectional images included in the second transmission information and then construct a rendered image, using the data processor 7300. This rendered image is, for example, a front image similar to a transillumination image. The image interpretation processor 7100 performs interpretation of the rendered image. For example, the image interpretation processor 7100 executes for example, the process of evaluating the grade of cataract by performing image interpretation of a front image similar to a transillumination image. The image interpretation apparatus 7000*m* transmits, using means of the communication device 7200 (a transmission device), the fourth transmission information that includes information generated by the image interpretation processor 7100, to the server 4000 via the communication line 1100.

The server 4000 receives the fourth transmission information transmitted from the image interpretation apparatus 7000*m* using the communication device 4200 (a reception device), associates the fourth transmission information with the first transmission information, and stores the fourth transmission information in the memory 4110.

As can be seen from the effects of the first aspect example, the ophthalmic system 1000A thus configured is capable of appropriately performing automatic image interpretation based on the image of the anterior segment acquired in advance. The acquisition of the image of the anterior segment may be performed at a remote place. With a conventional technology, a doctor conducts a medical examination while operating a slit lamp microscope from a remote place, however, according to the present aspect example, a doctor only needs to conduct image interpretation while referring to a result of the automatic image interpretation performed based on the images acquired in advance. In other words, according to the present aspect example, a doctor can be made free from the time and effort required for conducting photography, and the result of the automatic image interpretation can be provided to the doctor, which can greatly improve the efficiency of the image interpretation task. In addition, the present example is also expected to improve the accuracy of image interpretation. Therefore, the present aspect example contributes to expanding the area to which a high quality slit lamp microscope examination can be provided.

<Some Additional Matters and Items>

Figure 14:
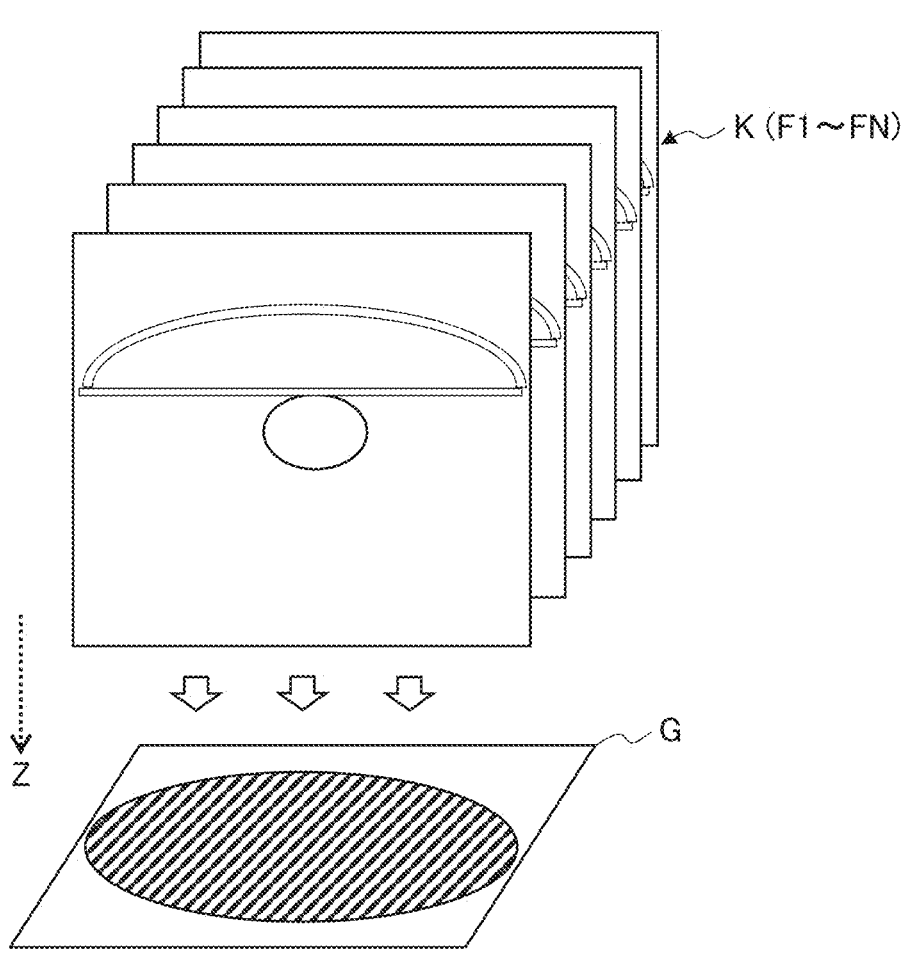
FIG. 14 is a schematic diagram for describing a rendering process of the aspect example.

Some examples of rendering performed in some aspect examples will be described. FIG. 14 shows an example of rendering for constructing a projection image defined on the XY plane. The reference character K denotes a three dimensional reconstructed image (e.g., stack data) constructed from the plurality of anterior segment images F1 to FN shown in FIG. 3. The rendering processor of some aspect examples applies projection in the Z direction to this three dimensional reconstructed image K. As a result of this, the rendered image (projection image) G defined on the XY plane perpendicular to the Z direction is constructed.

Figure 15:
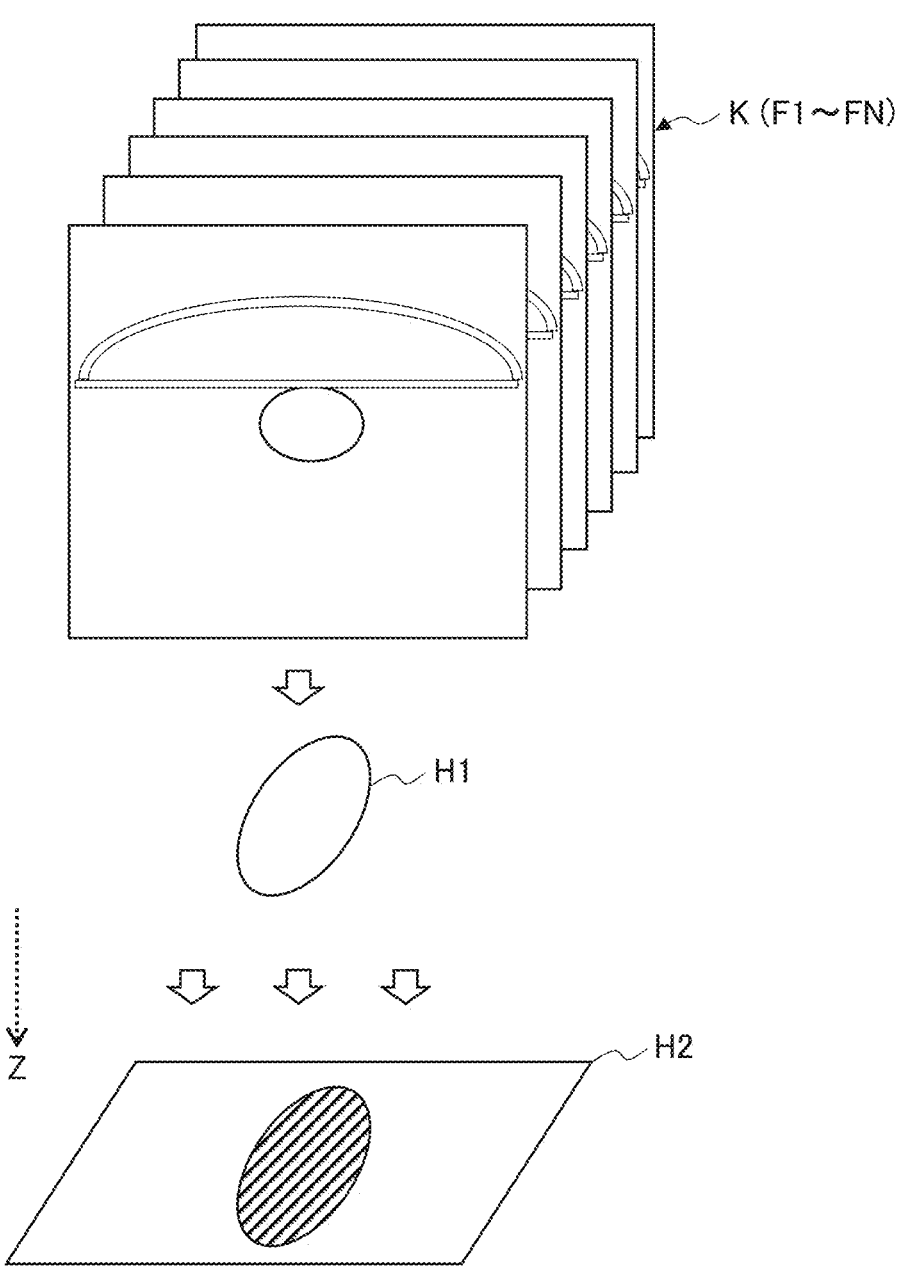
FIG. 15 is a schematic diagram for describing a rendering process of the aspect example.

FIG. 15 shows another example of rendering for constructing a projection image defined on the XY plane. The segmentation processor of some aspect examples extracts the crystalline lens region H1 from the three dimensional reconstructed image K constructed from the plurality of anterior segment images F1 to FN. The crystalline lens region H1 is a three dimensional image. The rendering processor of some aspect examples applies projection in the Z direction to the crystalline lens region H1. As a result of this, the rendered image (projection image) H2 of the crystalline lens region H1 is constructed. This rendered image H2 is defined on the XY plane perpendicular to the Z direction.

The present disclosure provides a method of controlling a slit lamp microscope in accordance with any of the aspect examples described above. This slit lamp microscope includes a processor and a scanner. The scanner is configured to perform scanning on the anterior segment of a subject's eye with slit light, thereby collecting a plurality of cross sectional images. The control method of the present aspect example causes the processor to execute a process of applying rendering to a three dimensional image created based on the plurality of cross sectional images collected by the scanner.

The present disclosure provides a program that causes a computer to execute the control method described above. In addition, the present disclosure provides a computer-readable non-transitory recording medium that stores this program. The non-transitory recording medium may be in any form, and examples of the non-transitory recording medium include a magnetic disk, an optical disk, a magneto-optical disk, and a semiconductor memory.

Similarly, the present disclosure can provide any control method described in any of the first to the fourth aspect examples. Further, the present disclosure can provide any processing method (e.g., arithmetic method, calculating method, image processing method, image analysis method, etc.) described in any of the first to the fourth aspect examples. Furthermore, the present disclosure can provide a program that causes a computer to execute such a processing method. In addition, the present disclosure can provide a computer-readable non-transitory recording medium in which such a program is stored.

Some aspect examples described above are merely examples of the implementation of the present disclosure, and any modifications (e.g., omission, substitution, replacement, addition, etc.) may be made within the scope of the present disclosure to the above aspect examples.

What is claimed is:

1. A slit lamp microscope comprising:
   a scanner configured to scan a crystalline lens including opaque areas of an anterior segment of a subject's eye with slit light to collect a plurality of cross sectional images;
   a reconstruction processor configured to apply three dimensional reconstruction to the plurality of cross sectional images collected by the scanner;
   a segmentation processor configured to apply segmentation to a three dimensional reconstructed image constructed by the reconstruction processor to identify a crystalline lens region corresponding to at least part of the crystalline lens from the three dimensional reconstructed image;

a rendering processor configured to apply rendering to the crystalline lens region in which the opaque areas are depicted; and a controller, wherein the scanner includes an illumination system configured to project the slit light onto at least the crystalline lens, a photography system configured to perform photography of at least the crystalline lens from a direction different from the illumination system, and a movement mechanism configured to move the illumination system and the photography system, the controller is configured to control the illumination system to perform adjustment of intensity of the slit light, wherein the photography system includes an optical system configured to direct light coming from the anterior segment onto which the slit light is projected, and an image sensor including a light detecting plane configured to receive the light directed by the optical system, wherein a subject plane along an optical axis of the illumination system, the optical system, and the light detecting plane satisfy a Scheimpflug condition, and the scanner is configured to scan the crystalline lens in a state in which focus of the photography system is on an entirety of at least an area from a cornea of the anterior segment to the crystalline lens by adjusting relative positions of the illumination system and the photography system using the movement mechanism.

2. The slit lamp microscope of claim 1, wherein the rendering processor is configured to apply projection onto a predetermined plane to the crystalline lens region.

3. The slit lamp microscope of claim 2, wherein the predetermined plane is perpendicular to a depth direction of the subject's eye.

4. The slit lamp microscope of claim 1, wherein the segmentation processor is configured to apply segmentation to the crystalline lens region to identify a partial region that has a dimension in a depth direction of the subject's eye, and the rendering processor is configured to apply the rendering to the partial region.

5. The slit lamp microscope of claim 4, wherein the segmentation processor is configured to identify at least one region of a capsule region and a nucleus region from the crystalline lens region, and identify the partial region based on the at least one region.

6. The slit lamp microscope of claim 1, further comprising a display device that displays a rendered image constructed by the rendering processor.

7. The slit lamp microscope of claim 1, wherein the controller is further configured to control the photography system to perform sensitivity adjustment.

8. The slit lamp microscope of claim 1, wherein the adjusting relative positions of the illumination system and the photography system is performed using the movement mechanism to adjust an angle formed by the optical axes of the illumination system and the photography system.

9. An ophthalmic system comprising a slit lamp microscope, an information processing apparatus, and an image interpretation computer terminal, wherein the slit lamp microscope includes:

a controller;

a scanner configured to scan a crystalline lens including opaque areas of an anterior segment of a subject's eye with slit light to collect a plurality of cross sectional images, the scanner including an illumination system configured to project the slit light onto at least the crystalline lens, a photography system configured to perform photography of the crystalline lens from a direction different from the illumination system, and a movement mechanism configured to move the illumination system and the photography system, and the controller is configured to control the illumination system to perform adjustment of intensity of the slit light; and a transmission device that transmits first transmission information that includes at least the plurality of cross sectional images collected by the scanner to the information processing apparatus via a communication line, the information processing apparatus includes:

a reception device that receives the first transmission information, a memory in which the first transmission information is stored; and a transmission device that transmits second transmission information that includes at least the plurality of cross sectional images included in the first transmission information to the image interpretation computer terminal via a communication line, and the image interpretation computer terminal includes:

a reception device that receives the second transmission information;

a rendering processor configured to apply rendering to a three dimensional image, in which the opaque areas are depicted, created from the plurality of cross sectional images included in the second transmission information;

a user interface operated by a user to perform interpretation of a rendered image constructed by the rendering processor, and a transmission device that transmits third transmission information that includes at least information input using the user interface to the information processing apparatus via a communication line, wherein the information processing apparatus receives the third transmission information by the reception device thereof, associates the third transmission information with the first transmission information, and stores the third transmission information in the memory, and the ophthalmic system further comprising:

a reconstruction processor configured to apply three dimensional reconstruction to the plurality of cross sectional images collected by the scanner; and a segmentation processor configured to apply segmentation to a three dimensional reconstructed image constructed by the reconstruction processor to identify a crystalline lens region corresponding to at least part of the crystalline lens from the three dimensional reconstructed image, wherein the rendering processor is further configured to apply rendering to the crystalline lens region in which the opaque areas are depicted, wherein the photography system includes an optical system configured to direct light coming from the anterior segment onto which the slit light is projected, and an image sensor including a light detecting plane configured to receive the light directed by the optical system, wherein a subject plane along an optical axis of the illumination system, the optical system, and the light detecting plane satisfy a Scheimpflug condition, and

the scanner is configured to scan the crystalline lens in a state in which focus of the photography system is on an entirety of at least an area from a cornea of the anterior segment to the crystalline lens by adjusting relative positions of the illumination system and the photography system using the movement mechanism.

10. An ophthalmic system comprising a slit lamp microscope, an information processing apparatus, and an image interpretation apparatus, wherein
the slit lamp microscope includes:
a controller;
a scanner configured to scan a crystalline lens including opaque areas of an anterior segment of a subject's eye with slit light to collect a plurality of cross sectional images, the scanner including an illumination system configured to project the slit light onto at least the crystalline lens, a photography system configured to perform photography of at least the crystalline lens from a direction different from the illumination system, and a movement mechanism configured to move the illumination system and the photography system, and the controller is configured to control the illumination system to perform adjustment of intensity of the slit light; and
a transmission device that transmits first transmission information that includes at least the plurality of cross sectional images collected by the scanner to the information processing apparatus via a communication line,
the information processing apparatus includes:
a reception device that receives the first transmission information;
a memory in which the first transmission information is stored; and
a transmission device that transmits second transmission information that includes at least the plurality of cross sectional images included in the first transmission information to the image interpretation apparatus via a communication line, and
the image interpretation apparatus includes:
a reception device that receives the second transmission information;
a rendering processor configured to apply rendering to a three dimensional image, in which the opaque areas are depicted, created from the plurality of cross sectional images included in the second transmission information;
an image interpretation processor configured to perform interpretation of a rendered image constructed by the rendering processor; and
a transmission device that transmits fourth transmission information that includes at least information generated by the image interpretation processor to the information processing apparatus via a communication line,
wherein the information processing apparatus receives the fourth transmission information by the reception device thereof, associates the fourth transmission information with the first transmission information, and stores the fourth transmission information in the memory, and
the ophthalmic system further comprising:
a reconstruction processor configured to apply three dimensional reconstruction to the plurality of cross sectional images collected by the scanner; and
a segmentation processor configured to apply segmentation to a three dimensional reconstructed image constructed by the reconstruction processor to identify a crystalline lens region corresponding to at least part of the crystalline lens from the three dimensional reconstructed image,
wherein the rendering processor is further configured to apply rendering to the crystalline lens region in which the opaque areas are depicted,
wherein the photography system includes an optical system configured to direct light coming from the anterior segment onto which the slit light is projected, and an image sensor including a light detecting plane configured to receive the light directed by the optical system,
wherein a subject plane along an optical axis of the illumination system, the optical system, and the light detecting plane satisfy a Scheimpflug condition, and
the scanner is configured to scan the crystalline lens in a state in which focus of the photography system is on an entirety of at least an area from a cornea of the anterior segment to the crystalline lens by adjusting relative positions of the illumination system and the photography system using the movement mechanism.

11. A method of controlling a slit lamp microscope that includes a processor, a controller, and a scanner, the method comprising:
causing the scanner to scan a crystalline lens including opaque areas of an anterior segment of a subject's eye with slit light to collect a plurality of cross sectional images, the scanner including an illumination system configured to project the slit light onto at least the crystalline lens, a photography system configured to perform photography of at least the crystalline lens from a direction different from the illumination system, and a movement mechanism configured to move the illumination system and the photography system;
causing the processor to execute a process of applying three dimensional reconstruction to the plurality of cross sectional images collected by the scanner;
causing the processor to execute a process of segmentation to a three dimensional reconstructed image constructed by the three dimensional reconstruction to identify a crystalline lens region corresponding to at least part of the crystalline lens from the three dimensional reconstructed image;
causing the processor to execute a process of applying rendering to the crystalline lens region in which the opaque areas are depicted; and
causing the controller to control the illumination system to perform adjustment of intensity of the slit light,
wherein the photography system includes an optical system configured to direct light coming from the anterior segment onto which the slit light is projected, and an image sensor including a light detecting plane configured to receive the light directed by the optical system,
wherein a subject plane along an optical axis of the illumination system, the optical system, and the light detecting plane satisfy a Scheimpflug condition, and
the method further includes causing the scanner to scan the crystalline lens in a state in which focus of the photography system is on an entirety of at least an area from a cornea of the anterior segment to the crystalline lens by adjusting relative positions of the illumination system and the photography system using the movement mechanism.

12. A computer-readable non-transitory recording medium storing a program configured to cause a computer to execute the method of claim 11.

\* \* \* \* \*